United States Patent
Liu et al.

(10) Patent No.: US 10,393,695 B2
(45) Date of Patent: Aug. 27, 2019

(54) INTEGRATED CIRCUIT DEVICE WITH ADAPTATIONS FOR MULTIPLEXED BIOSENSING

(71) Applicant: Taiwan Semiconductor Manufacturing Co., Ltd., Hsinchu (TW)

(72) Inventors: Yi-Shao Liu, Zhubei (TW); Jui-Cheng Huang, Hsinchu (TW); Tung-Tsun Chen, Hsinchu (TW)

(73) Assignee: Taiwan Semiconductor Manufacturing Co., Ltd. (TW)

( * ) Notice: Subject to any disclaimer, the term of this patent is extended or adjusted under 35 U.S.C. 154(b) by 0 days.

(21) Appl. No.: 16/165,748

(22) Filed: Oct. 19, 2018

(65) Prior Publication Data
US 2019/0056348 A1    Feb. 21, 2019

Related U.S. Application Data

(63) Continuation of application No. 15/492,548, filed on Apr. 20, 2017, now Pat. No. 10,139,364, which is a
(Continued)

(51) Int. Cl.
*H01L 21/00* (2006.01)
*G01N 27/414* (2006.01)
(Continued)

(52) U.S. Cl.
CPC ..... *G01N 27/4148* (2013.01); *G01N 27/4145* (2013.01); *H01L 23/345* (2013.01);
(Continued)

(58) Field of Classification Search
None
See application file for complete search history.

(56) References Cited

U.S. PATENT DOCUMENTS 5,702,981 A    12/1997  Maniar et al.
7,060,510 B2    6/2006  Bonnell et al.
(Continued)

OTHER PUBLICATIONS

Bhattacharya, et al.; "PCR-Based Detection in a Micro-Fabricated Platform;" Lab Chip; The Royal Society of Chemistry; 2008; p. 1130-1136.
(Continued)

*Primary Examiner* — Hung K Vu
(74) *Attorney, Agent, or Firm* — Sterne, Kessler, Goldstein & Fox P.L.L.C.

(57) ABSTRACT

A method of manufacturing an integrated circuit device includes providing a substrate comprising a semiconductor active layer, and forming source/drain regions, temperature sensors, and heating elements either in the semiconductor active layer or on the front side of the semiconductor active layer. The semiconductor active layer has channel regions between adjacent source/drain regions, and each of the heating elements is aligned over at least a portion of a corresponding temperature sensor. The method also includes forming a metal interconnect structure over the front side of the semiconductor active layer and exposing the channel regions from the back side of the semiconductor active layer substrate. A fluid gate dielectric layer is formed over the exposed channel regions.

20 Claims, 14 Drawing Sheets

Related U.S. Application Data continuation of application No. 14/713,543, filed on May 15, 2015, now Pat. No. 9,709,524.

(51) Int. Cl.
  *H01L 23/34* (2006.01)
  *H01L 27/085* (2006.01)
  *H01L 27/16* (2006.01)
  *H01L 27/02* (2006.01)

(52) U.S. Cl.
  CPC ............ *H01L 27/085* (2013.01); *H01L 27/16* (2013.01); *H01L 27/0211* (2013.01)

(56) References Cited

U.S. PATENT DOCUMENTS

| | | | |
|---|---|---|---|
| 7,306,924 | B2 | 12/2007 | Gomez et al. |
| 7,632,670 | B2 | 12/2009 | Offenhausser et al. |
| 7,695,609 | B2 | 4/2010 | Soundarrajan et al. |
| 7,696,530 | B2 | 4/2010 | Yamamoto et al. |
| 7,728,401 | B2 | 6/2010 | Takatori |
| 7,833,708 | B2 | 11/2010 | Enzelberger et al. |
| 7,923,314 | B2 | 4/2011 | Tezuka et al. |
| 7,948,041 | B2 * | 5/2011 | Bryant ................ G01N 27/127 257/414 |
| 8,007,727 | B2 | 8/2011 | Shalev et al. |
| 8,110,883 | B2 * | 2/2012 | Ward ...................... G01J 5/02 257/428 |
| 8,405,169 | B2 | 3/2013 | Cheng et al. |
| 8,420,328 | B2 | 4/2013 | Chen et al. |
| 8,471,559 | B2 | 6/2013 | Taherian et al. |
| 8,519,490 | B2 | 8/2013 | Bikumandla |
| 8,557,643 | B2 | 10/2013 | Han et al. |
| 8,569,808 | B1 | 10/2013 | Chen et al. |
| 8,728,844 | B1 | 5/2014 | Liu et al. |
| 8,762,925 | B2 | 6/2014 | Chen et al. |
| 8,778,269 | B2 | 7/2014 | Joshi et al. |
| 8,791,557 | B2 | 7/2014 | Chang et al. |
| 8,846,416 | B1 | 9/2014 | Chu et al. |
| 8,871,549 | B2 | 10/2014 | Ellis-Monaghan et al. |
| 8,878,258 | B2 | 11/2014 | Monfray et al. |
| 9,080,969 | B2 | 7/2015 | Liu et al. |
| 9,389,199 | B2 | 7/2016 | Cheng et al. |
| 9,417,209 | B2 | 8/2016 | Shen et al. |
| 9,709,524 | B2 | 7/2017 | Liu et al. |
| 2006/0197118 | A1 | 9/2006 | Migliorato et al. |
| 2010/0055699 | A1 * | 3/2010 | Kahya ................ G01N 27/4145 435/6.19 |
| 2010/0230578 | A1 | 9/2010 | Horikoshi et al. |
| 2012/0021918 | A1 | 1/2012 | Bashir et al. |
| 2012/0032235 | A1 | 2/2012 | Bikumandla |
| 2013/0105868 | A1 | 5/2013 | Kalnitsky et al. |
| 2013/0200438 | A1 | 8/2013 | Liu et al. |
| 2013/0256259 | A1 | 10/2013 | Chang et al. |
| 2013/0293878 | A1 | 11/2013 | Chang et al. |
| 2014/0073039 | A1 | 3/2014 | Chang et al. |
| 2014/0134748 | A1 | 5/2014 | Liu et al. |
| 2014/0225166 | A1 | 8/2014 | Ellis-Monaghan et al. |
| 2014/0256030 | A1 | 9/2014 | Shen et al. |
| 2014/0264467 | A1 | 9/2014 | Cheng et al. |
| 2014/0264468 | A1 | 9/2014 | Cheng et al. |
| 2014/0335640 | A1 | 11/2014 | Chang et al. |
| 2014/0370636 | A1 | 12/2014 | Dalton et al. |
| 2015/0129937 | A1 | 5/2015 | Chen et al. |
| 2016/0209355 | A1 | 7/2016 | Tseng et al. |
| 2016/0334362 | A1 | 11/2016 | Liu et al. |
| 2016/0341656 | A1 | 11/2016 | Liu et al. |
| 2017/0219520 | A1 | 8/2017 | Liu et al. |
| 2017/0343498 | A1 | 11/2017 | Kalnitsky et al. |

OTHER PUBLICATIONS

Dametto, Paolo; "DNA Amplification and Detection Using a pH-Sensing System: Implications for Current Analytical Technologies and Point-of-Care Nucleic Acid Tests;" Aug. 2013; p. 1-31.

Jang, et al. "Performance Enhancement of Capacitive-Coupling Dual-Gate Ion-Sensitive Field-Effect Transistor in Ultra-Thin-Body." Scientific Reports, 4:5284. Published Jun. 13, 2014.

Lee, et al.; "Microchip-based one step DNA Extraction and Real-Time PCR in one Chamber for Rapid Pathogen Identification;" Lab Chip; The Royal Society of Chemistry 2006; p. 886-895.

Mandavifar, et al. "Implementation of a Polysilicon Micro Electro-Thermal Detector in Gas Chromatography System with Applications in Portable Environmental Monitoring." ECS Journal of Solid State Science and Technology, 4 (10) S3062-S3066 (2015). Aug. 28, 2015.

Nanohelix.net RealHelix qPCR Kit. Published in 2009. Retrieved online at http://www.nanohelix.net/02_products/view.asp?pack_code=277.

Petrucci, et al. "Thermal Characterization of Thin Film Heater for Lab-On-Chip Application." 2015 XVIII AISEM Annual Conference. Feb. 2015.

Romero-Garcia, et al.; "Silicon Nitride CMOS-compatible Platform for Integrated Photonics Applications at Visible Wavelengths;" Optics Express, vol. 21, No. 12, Jun. 17, 2013, p. 1-11.

Salm, et al. "Ultralocalized Thermal Reactions in Subnanoliter Droplets-in-air;" PNAS; vol. 110; No. 9; Feb. 26, 2013; p. 3310-3315.

Scorzoni, et al. "Thermal Characterization of a Thin Film Heater on Glass Substrate for Lab-on-Chip Applications." 2014 IEEE International Instrumentation and Measurement Technology Conference (I2MTC) Proceedings. May 12, 2014.

"Supporting Information for Ultra localized Thermal Reactions in Subnanoliter Droplets-in-air;" PNAS, vol. 110; No. 9, Feb. 26, 2013, p. 1-25.

Toumazou, et al. "Simultaneous DNA amplification and detection using a pH-sensing semiconductor system." Nature Methods, vol. 10, No. 7, Jul. 2013.

\* cited by examiner

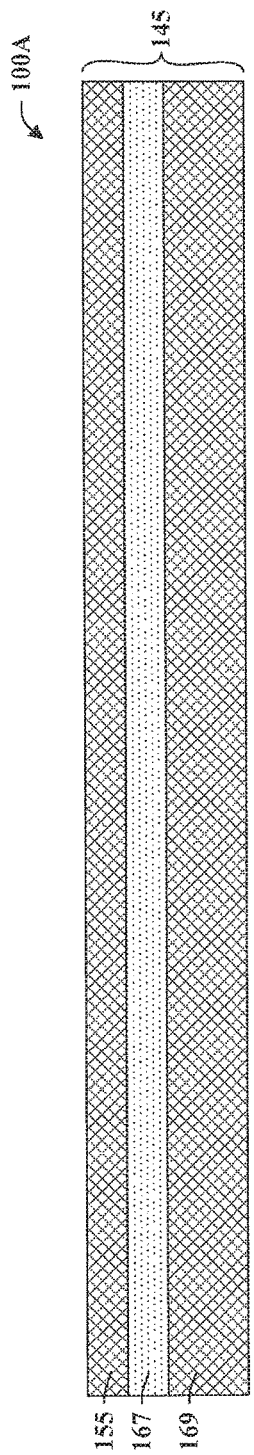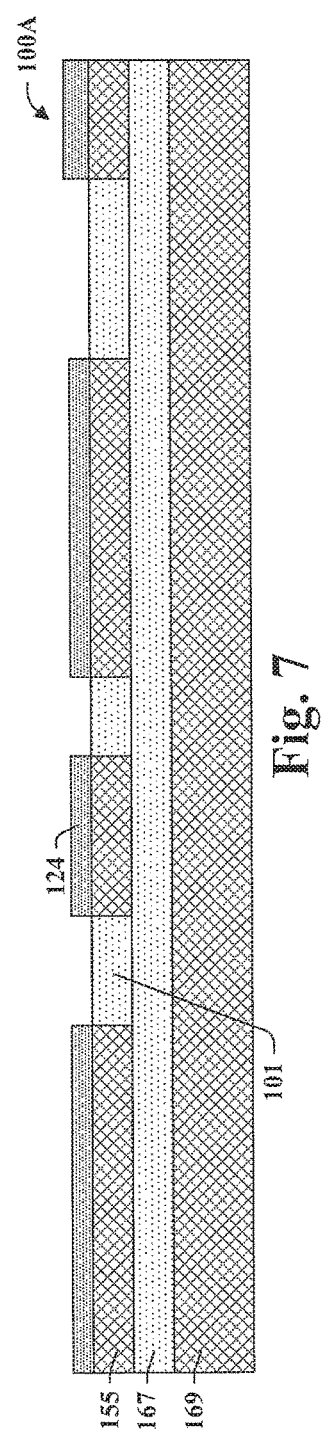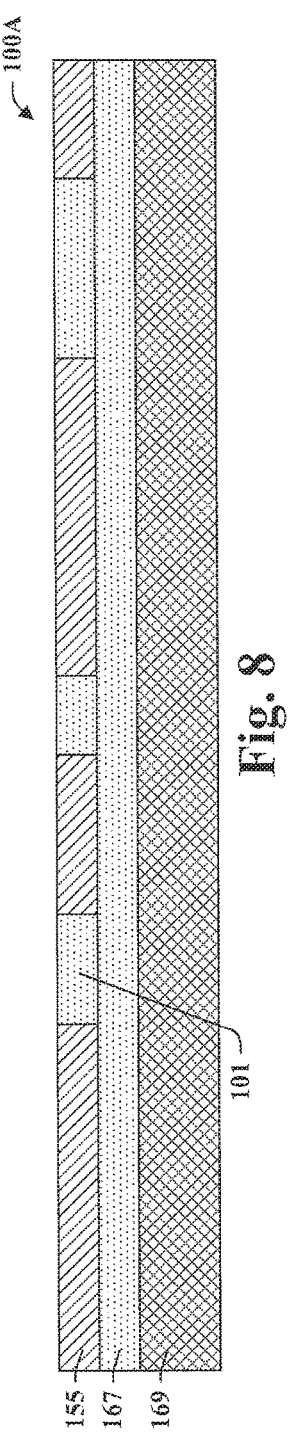

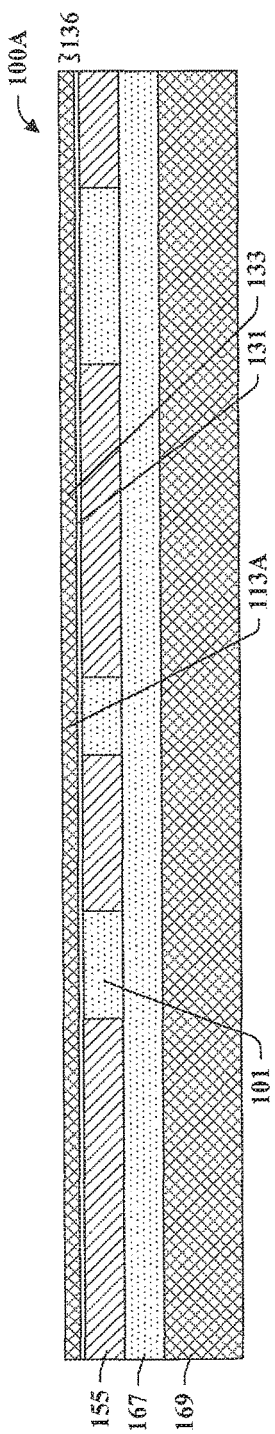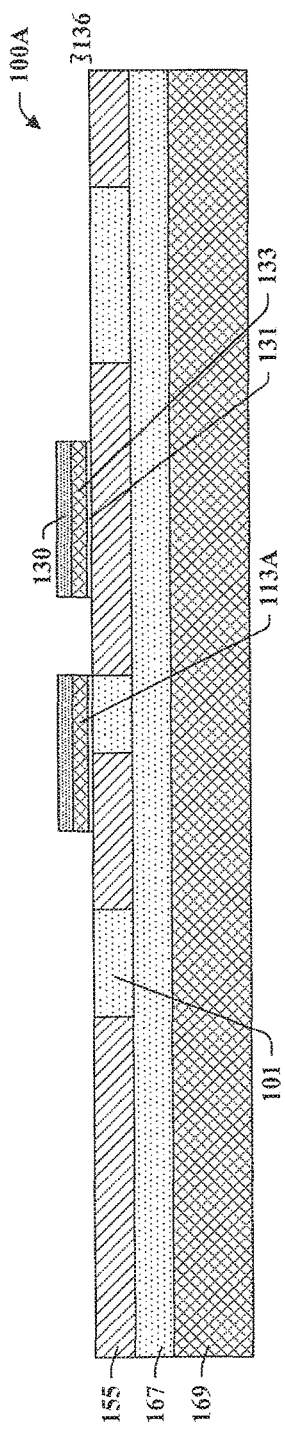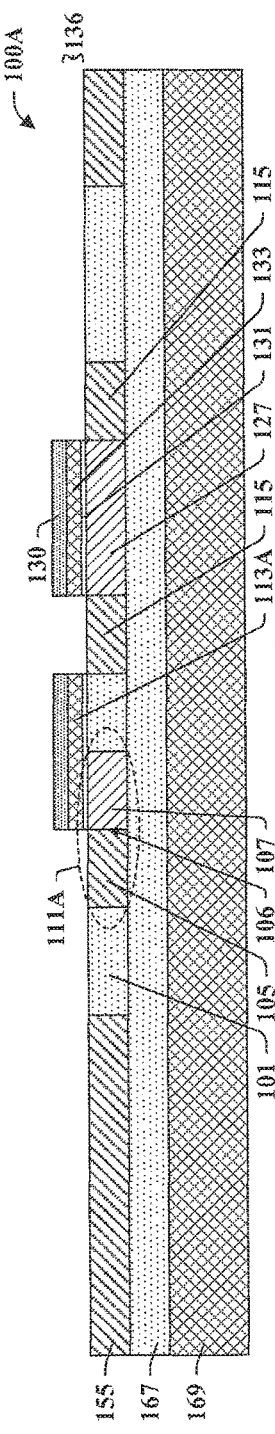

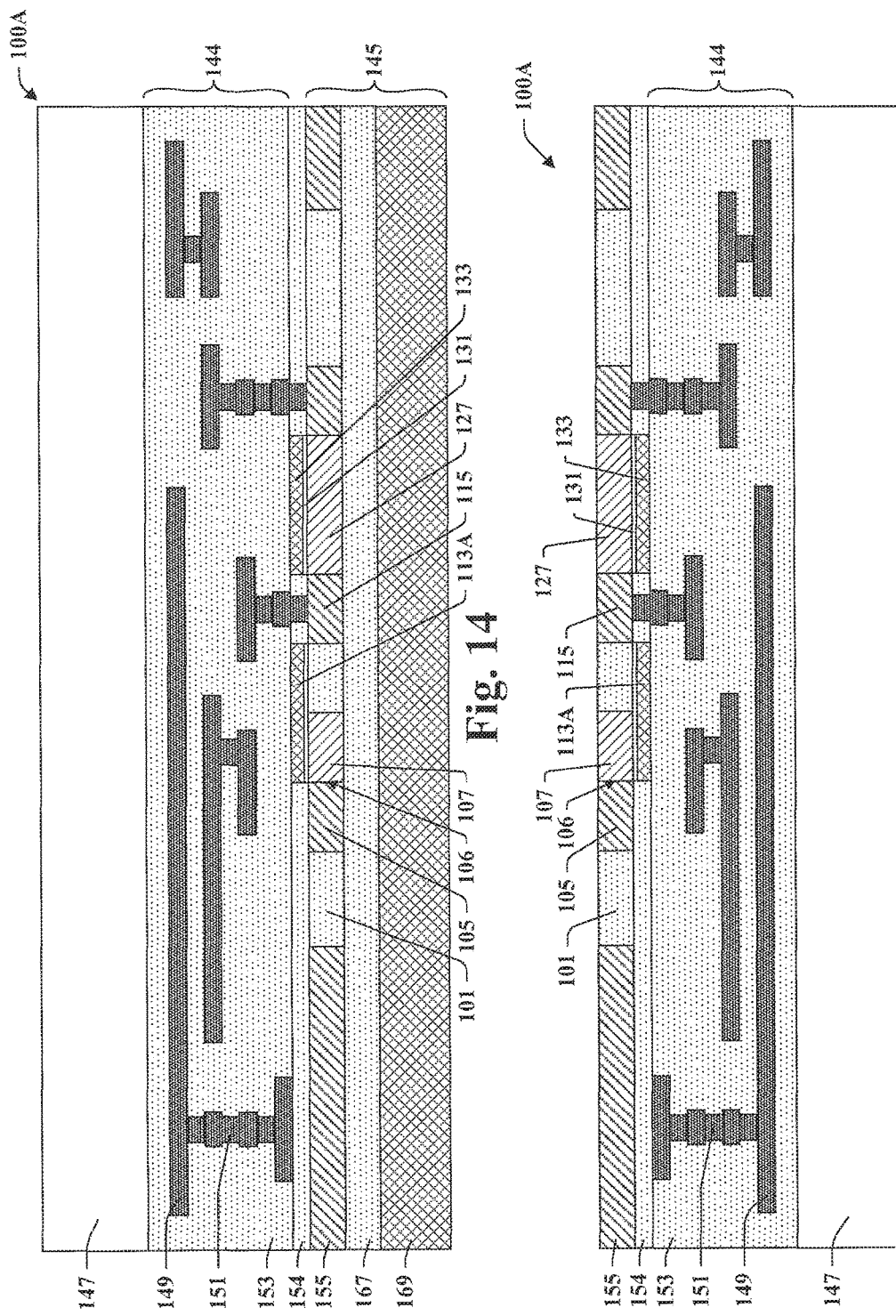

INTEGRATED CIRCUIT DEVICE WITH ADAPTATIONS FOR MULTIPLEXED BIOSENSING

CROSS-REFERENCE TO RELATED APPLICATION

This application is a continuation of U.S. application Ser. No. 15/492,548, filed on Apr. 20, 2017, which is a continuation of U.S. application Ser. No. 14/713,543, filed on May 15, 2015 (now U.S. Pat. No. 9,709,524), the disclosures of which are incorporated herein by reference in their entireties.

BACKGROUND

Integrated circuit devices can be adapted to detect biological markers. One such adaptation is the inclusion of bioFETs (biologically sensitive field effect transistors). As the term is used herein, a bioFET is a transistor that can be switched by being placed in contact with a liquid having a suitable composition. A suitable composition can include the presence of certain suspended solids, such as particular types of cells or biomolecules. The portion of the transistor configured to interface with the liquid is referred to as a fluid gate. A bioFET can be a dual gate transistor that includes a conventional gate, such as a gate having a polysilicon electrode. The conventional gate can be located on an opposite side of the transistor channel from the fluid gate. In such a configuration, the conventional gate can be used to modulate the effect that charge on the fluid gate has on the conductivity of the transistor channel.

BRIEF DESCRIPTION OF THE DRAWINGS

Aspects of the present disclosure are best understood when read with the accompanying figures. In accordance with standard practice in the industry, various features are drawn without scaling proportionally. Some dimensions of some features may be increased or decreased relative to others for clarity in the figures.

FIGS. 6-21 are cross-sectional schematic illustrations of a device according to some embodiments of the present disclosure being manufactured by a method according to some embodiments of the present disclosure.

DETAILED DESCRIPTION

Figure 1A:
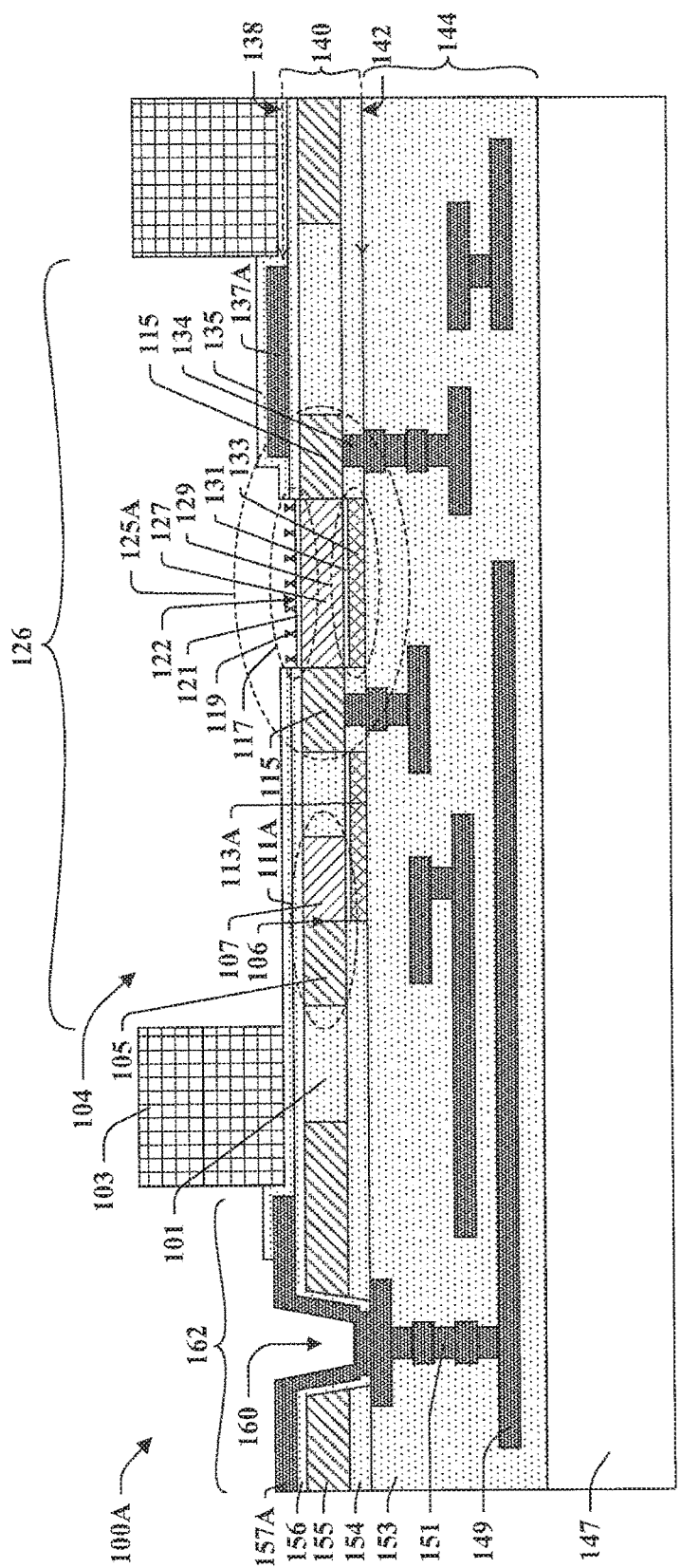
FIG. 1A is a schematic illustration of an integrated circuit device in accordance with some embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

It is desirable for a biosensor to be capable of screening for multiple analytes. A challenge to implementing such multiplexed detection is that many analytic methods require controlled variations in temperature. The required temperatures can vary according to analyte or analytic method. The challenge is made greater in that the small size of integrated circuit devices makes heat tend to spread across them rapidly. The present disclosure meets this challenge with an integrated circuit device in which heaters and temperature sensors are formed into a device layer that also includes bioFETs. The integrated circuit device can be operational to heat fluids and control fluid temperatures independently among a plurality of small volumes adjacent differing localities on the device. Localized heating can be facilitated by forming a multilayer metal interconnect structure on the opposite side of the device layer from the fluid gates of the bioFETs. In this configuration, the heating elements are located between the multilayer metal interconnect structure and the fluid so that the heat does not need to warm and diffuse through the multilayer metal interconnect structure to reach the fluid.

Figure 1B:
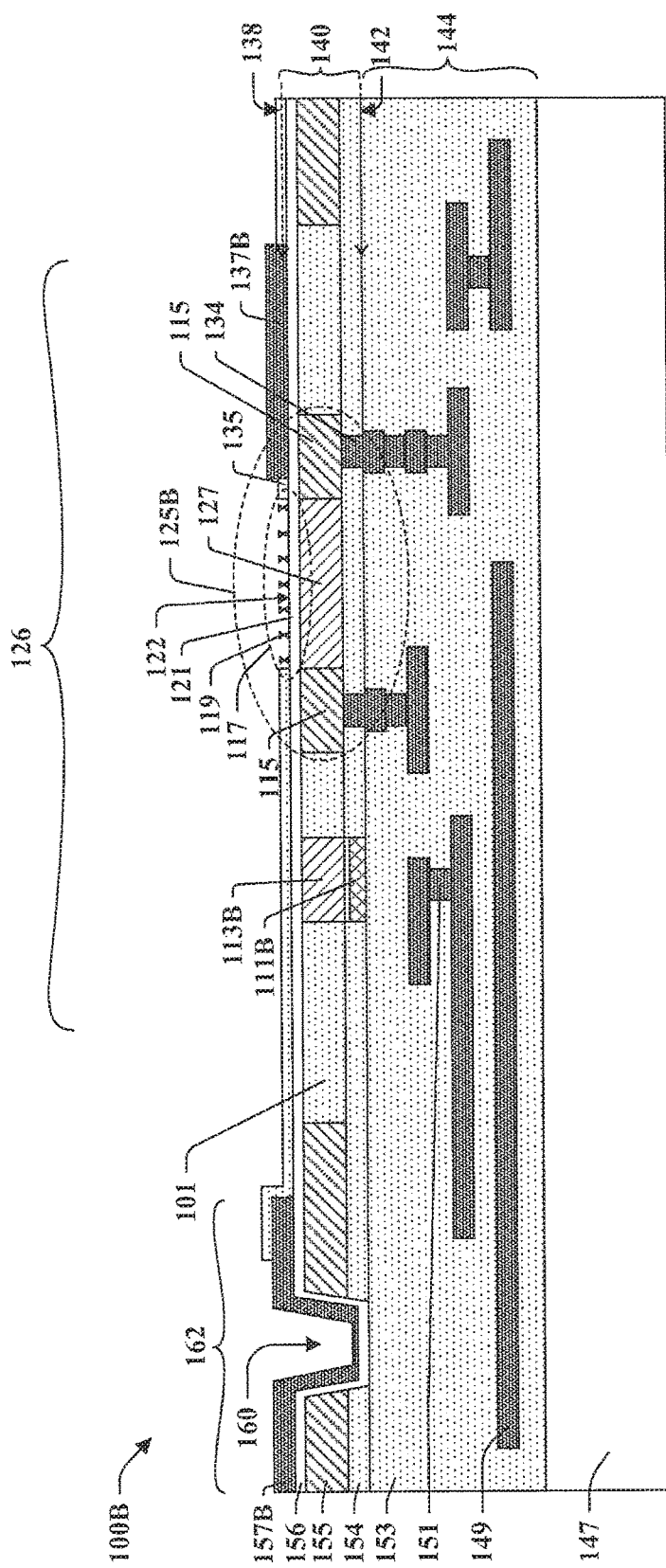
FIG. 1B is a schematic illustration of an integrated circuit device in accordance with some other embodiments of the present disclosure.

FIG. 1A provides an example device 100A according to some embodiments of the present disclosure. FIG. 1B provides another example device 100B illustrating a number of possible variations on the device 100A provided by the present disclosure. The device 100 (a generic reference inclusive of both device 100A and 100B, a convention followed for similar reference numerals throughout this description) includes a device layer 140. A device layer can be defined as a thin layer of an integrated circuit device including a semiconductor active layer and various devices that include components in the active layer or in close proximity to the active layer. A device layer can be the portion of an integrated circuit device extending downward through a semiconductor active layer to the depth of the transistor channels and upward to the lower limit of an overlying metal interconnect structure. For device 100A, device layer 140 includes semiconductor active layer 155, isolation regions 101, temperature sensors 111A, heating elements 113A, and bioFETs 125A. For device 100B, device layer 140 includes temperature sensors 111B, heating elements 113B, and bioFETs 125B. Device layer 140 can be approximately 1 μm or less in thickness. In some embodiments, active layer 155 is approximately 200 nm or less in thickness. In some embodiments, the devices of device layer 140 are within approximately 100 nm of active layer 155. In some embodiments, the devices of device layer 140 are contained within a zone extending approximately 400 nm above and approximately 400 nm below active layer 155. These dimensions can promote localized heating and precision temperature control.

Active layer 155 includes a semiconductor. In some embodiments, active layer 155 is formed from a single semiconductor crystal. In some embodiments, the semiconductor is silicon. Alternatively, the semiconductor can be another elementary semiconductor, such as germanium; a compound semiconductor such as silicon carbide, gallium arsenic, gallium phosphide, indium phosphide, indium arsenide, and/or indium antimonide; an alloy semiconductor such as SiGe, GaAsP, AlInAs, AlGaAs, GaInAs, GaInP, or GaInAsP; or a combinations thereof. In some embodiments, active layer 155 is doped to include n-doped regions and p-doped regions to provide a complementary metal oxide semiconductor device (CMOS).

Active layer 155 can be divided into a plurality of electrically and thermally isolated regions by isolation regions 101. Isolation regions 101 are dielectric. The dielectric can be an oxidized form of the semiconductor of active layer 155. In some embodiments, isolation regions 101 are shallow trench isolation regions.

Device 100 includes a plurality of device regions 126. In some embodiments, device 100 includes a plurality of device regions 126 that are one $mm^2$ or less in area. In some embodiments, device 100 includes a plurality of device regions 126 that are 0.1 $mm^2$ or less in area. In some embodiments, device 100 includes 100 or more device regions 126. In some embodiments, device 100 includes 1000 or more device regions 126. In some embodiments, device 100 is operative to control the temperature of each device region 126 independently.

Heating elements 113 are operable to control temperature in device regions 126 and in small volumes of liquid adjacent each of the device regions 126. In some embodiments, these volumes correspond to fluid containment areas 104. In some embodiments, there is one fluid containment areas 104 for each device region 126. A fluid containment area 104 can be a well or a length of channel bound by fluid channel walls 103. Device 100A of FIG. 1A provides an example. Fluid channel walls 103 can be formed of any suitable material. In some embodiments, fluid channel walls 103 are an elastomer. In some of these embodiments, the elastomer of polydimethylsiloxane (PDMS). In some embodiments, fluid containment areas 104 are capped to provide closed channels or reservoirs.

In some embodiments, device 100 is designed to receive fluid samples in the form of micro-droplets. In such embodiments, device 100 may be uncapped and without fluid channel walls 103. Device 100B of FIG. 1B provides an example. In some embodiments, heating elements 113 are operable to independently control the temperature of one liquid droplet for each device region 126. In some embodiments, heating elements 113 are operable to control the temperature of a droplet having a height in the range from approximately 25 to approximately 100 μm. This and like functional limitations assume a separate droplet is provided for each independent device region 126.

Temperature control can include heating and cooling. In some embodiments, a carrier substrate 147 is structured to facilitate rapid cooling when heating discontinues. A structure that facilitates rapid cooling can include a thermal mass that is large in comparison to the liquid capacity of fluid containment areas 104. In some embodiments, the cooling rate is over 100° C./s when the peak temperature within the heated volume is 50° C. above ambient. In some of these embodiments, the cooling rate is over 500° C./s when the peak temperature within the heated volume is 50° C. above ambient. For devices 100 in which fluid containment areas 104 are absent or not enclosed, these and other liquid volume-dependent criteria are applicable to liquid covering device regions 126 to a depth of 50 μm.

High heating rates are desirable both to overcome cooling effects and to rapidly take liquid samples to desired temperatures. In some embodiments, heating elements 113 are operative to heat liquid in fluid containment areas 104 to 20° C. above ambient. In some of these embodiments, heating elements 113 are operative to heat liquid in fluid containment areas 104 to 60° C. above ambient. In some embodiments, heating elements 113 are operative to heat liquid in fluid containment areas 104 at a rate of 50° C./s or more. In some embodiments, heating elements 113 are operative to heat liquid in fluid containment areas 104 at a rate of 200° C./s or more.

Heating elements 113 can be resistive elements coupled to a suitable current supply. The heating rate is generally proportional to sheet resistance and to current density squared. However, because the device 100 is an integrated circuit device, there may be a practical limit on current density. In some embodiments, heating elements 113 are supplied with current through multilayer metal interconnect structure 144. To provide the desired heating rate while limiting current density, in some embodiments the sheet resistance of heating elements 113 is at least 1Ω/□. In some embodiments, the sheet resistance of heating elements 113 is at least 5Ω/□.

Because the sheet resistance of metals is generally 0.1Ω/□ or less, in some embodiments heating elements 113 are non-metal. The sheet resistance of semiconductors is tunable through doping. By suitable choice of semiconductor and doping, a semiconductor can be provided having a sheet resistance anywhere in the range from 1Ω/□ to $1 \times 10^3$ Ω/□. Accordingly, in some embodiments, heating elements 113 are semiconductors. In some embodiments, heating elements 113 are doped polysilicon. In some embodiments, bioFETs 125 include conventional gate electrodes 133 and heating elements 113 have the same thickness and composition as gate electrodes 133. Heating elements 113A of FIG. 1A provide an example. In some embodiments, the composition is polysilicon.

In some embodiments, heating elements 113 are formed by doping active layer 155. In some embodiments, heating elements 113 are formed together with source/drain regions 115 and have the same dopant concentration profile within active layer 155. Heating elements 113B of FIG. 1B provide an example.

Temperature sensors 111 can be disposed in or adjacent active layer 155 and can be any suitable type of temperature sensor. The output queried can be voltage, current, or resistance. In some embodiments, temperature sensors 111 include one or more diodes. In some embodiments, temperature sensors 111 include at least one P-N junction 106 forming a diode within active layer 155. The P-N junction 106 comprises a first diode regions 105 and second diode regions 107 having opposite conductivity types. Temperature sensor 111A of FIG. 1A provides an example. In some embodiments, each temperature sensor 111 includes two diodes. A dual diode temperature sensor 111 can provide a high degree of precision. In some embodiments, two diodes of temperature sensor 111 are configured to be operated at different current densities for proportional to absolute temperature (PTAT) temperature sensing.

In some embodiments, temperature sensors 111 comprise resistors and measure temperature according to a relationship between resistance and temperature. In some of these embodiments, the resistive element is a doped region of active layer 155. The doped region can form a shallow diffusion resistor or a well diffusion resistor. In some embodiments the resistive element is polysilicon. In some embodiments, polysilicon resistors for temperature sensors 111 are formed over active layer 155. Temperature sensor 111B of FIG. 1B provides an example. In some embodiments, polysilicon resistors for temperature sensors 111 are formed together with polysilicon gate electrodes 133 for bioFETs 125A. In some embodiments, polysilicon resistors for temperature sensors 111 are formed together with heating elements 113.

In some embodiments, one or more heating elements 113 are configured to operate as temperature sensors 111. In some embodiments, temperature sensors 111 are coupled to analog to digital converters (ADCs) on device 100, whereby device 100 is operable to provide a digital output from temperature sensors 111.

BioFETs 125 include source/drain regions 115 and channel regions 127 that are formed in semiconductor active layer 155. BioFETs 125 include fluid gates 117. In some embodiments, fluid gates 117 are the only gates of bioFETs 125. BioFET 125B of FIG. 1B provides an example. In some embodiments, bioFETs 125 are dual gate transistors having conventional gates 129 opposite fluid gates 117. BioFET 125A of FIG. 1A provides an example. A conventional gate 129 includes a gate dielectric 131 and a gate electrode 133. In some embodiment, gate electrodes 133 are polysilicon. In some other embodiments, gate electrodes 133 are metal. In some embodiments gate dielectric 131 is $SiO_2$. In some other embodiments, gate dielectric 131 is a high-k dielectric. Conventional gates 129 can be operative to modulate the response of bioFETs 125 to charge on fluid gates 117. Source/drain regions 115 can extend through the full thickness of active layer 155 to facilitate functioning of fluid gates 117. In some embodiments, a device 100 includes both single gate bioFETs 125B and dual gate bioFETs 125A.

Fluid gates 117 include a fluid gate dielectric layer 121 and a fluid interfacing surface 122. Fluid interfacing surface 122 is exposed for contacting with fluid. Fluid gates 117 are operative to modulate the source to drain conductivity of bioFET 125 when contacted by a fluid having a suitable composition or carrying specific analytes. In some embodiments, fluid interfacing surface 122 is the surface of an ion sensing film. Fluid gate dielectric layer 121 itself can provide the ion sensing film. Examples of materials for gate dielectric layer 121 that provide the functionality of an ion sensing film include $HfO_2$, $SiO_2$, $Si_3N_4$, $Al_2O_3$, and $Ta_2O_5$. Ion sensing films become charged when brought in contact with an aqueous solution having a suitable ion concentration. Moreover, they can become sufficiently charged to switch the source/drain conductivity of bioFETs 125. In some embodiments, device 100 includes bioFETs 125 having ion sensing films functional to detect whether or not a solution is above or below a critical pH.

In some embodiments, fluid interfacing surface 122 includes a coating of a selective binding agent 119. A selective binding agent 119 is a biological composition having the property of selectively binding with a particular analyte. Many biological molecules and structures are charged. If a sufficient concentration of the analyte is bound on fluid interfacing surface 122, the overall charge concentration at fluid interfacing surface 122 can become sufficient to modulate the source to drain conductivity of bioFETs 125. In some embodiments, the selective binding agent 119 includes an antibody. In some embodiments, the selective binding agent 119 includes a single stranded nucleic acid. In some embodiments, the selective binding agent 119 includes an epitope that is the target of certain antibodies.

In some embodiments, fluid interfacing surface 122 is restricted to an area above channel region 127. In some of these embodiments, fluid gate dielectric layer 121 extends over a broader area, but in the area that is not above channel region 127, fluid gate dielectric layer 121 is covered by passivation layer 135. Device 100B of FIG. 1B provides an example. Covering areas of fluid gate dielectric layer 121 that are not directly above channel regions 127 can prevent analytes from binding in regions where they have little or no effect on the conductivity of channel region 127. Analytes may thereby be concentrated where they are effective for switching bioFETs 125.

In some embodiments, fluid interfacing surface 122 extends beyond the area of channel regions 127. In some of these embodiments, a conductor configured as a floating gate (e.g., a conductive material surrounded by dielectric material) is interposed between fluid interfacing surface 122 and fluid gate dielectric layer 121. This configuration can extend the contact area between a fluid gate 117 and a fluid. Charges on fluid interfacing surface 122 can alter the potential of the floating gate, which can extend an electric field across fluid gate dielectric layer 121 sufficient to alter the conductivity of channel region 127. However, the benefit of an extended fluid contacting area can easily be offset by the parasitic capacitance of the floating gate. Accordingly, in some embodiments, fluid gate 117 does not include a floating gate.

In some embodiments, fluid interfacing surface 122 is approximately 2 μm or less from active layer 155. A distance of 2 μm or less is desirable to achieve local heating using heating elements 113 in or on active layer 155 In some embodiments, fluid interfacing surface 122 is approximately 100 nm or less from channel region 127. A distance of 100 nm or less can make local heating more effective. In some embodiments, these distances correspond to the thickness of fluid gate dielectric layer 121. In some embodiments, fluid gate dielectric 121 is very thin. In this context, approximately 3 nm or less is considered. A very thin fluid gate dielectric 121 increases the sensitivity of bioFETs 125.

In some embodiments where bioFETs 125 are dual gate transistors having conventional gates 129 opposite fluid gates 117, the resistance of fluid gate dielectric layer 121 may be less the resistance of gate dielectric 131. Lower resistance can be achieved by making fluid gate dielectric layer 121 thinner and/or of a more conductive material. Making the resistance of fluid gate dielectric layer 121 smaller than the resistance of gate dielectric 131 may increase the sensitivity of bioFETs 125. In some embodiments the resistance of fluid gate dielectric layer 121 is approximately half or less that of gate dielectric 131. In some embodiments the resistance of fluid gate dielectric layer 121 is approximately one quarter or less that of gate dielectric 131.

In some embodiments, the structure of bioFETs 125 varies among device regions 126 to provide multiplexed detection. In some embodiments, some device regions 126 have bioFETs 125 having fluid interfacing surfaces 122 of different compositions from the fluid interfacing surfaces 122 of bioFETs 125 of other device regions 126. In some embodiments, bioFETs 125 in some of the device region 126 have an ion sensing film not found in the bioFETs 125 of another device region 126. In some embodiments, fluid interfacing surface 122 of bioFETs 125 in some of the device regions 126 include a selective binding agent 119 not found in at the fluid interfacing surfaces 122 of bioFETs 125 in others of the device region 126. In some embodiments, bioFETs 125 vary in structure to provide multiplexed detection within a single device region 126. In these embodiments, the bioFETs 125 within a single device region 126 can be adapted for testing with the same temperature protocol.

In some embodiments, at least some of the device regions 126 include manipulation electrodes 137. Manipulation electrodes 137 are operative to manipulate analytes in adjacent fluid or set the adjacent fluid to a reference potential. Manipulation electrodes 137 can be one of several different types. One type is covered by a passivation layer 135 (e.g., a passivating dielectric) and may be operative to manipulate analytes through an electric field. Manipulation electrode 137A of FIG. 1A provide an example. Manipulation electrode 137A may be a diversion electrode that is operative to concentrate analytes proximate bioFETs 125. In some embodiments, manipulation electrodes 137A are operative to exert a steady electric field on adjacent fluid, such as fluid in a fluid containment area 104. A steady electric field can concentrate charged compounds proximate bioFETs 125.

In some embodiments, manipulation electrodes 137A are operative to exert an oscillating electric field. In some embodiments, manipulation electrodes 137A are operative for dielectrophoresis (DEP). DEP can be useful for concentrating cell or cell parts proximate bioFETs 125. The geometry of the manipulation electrodes 137A and the frequency of field oscillation can be chosen to select for particular cells, cell parts, or the like. For example, in some embodiments manipulation electrodes 137A are provided in an interdigitated pattern wherein the lengths of the electrodes are selected in part according to the desired selectivity.

If manipulation electrodes 137A are used for DEP or the like, analytes may tend to concentrate along the edges of manipulation electrodes 137A. Accordingly, in some embodiments, manipulation electrodes 137A are provided in strips having edges and bioFETs 125 are arranged along those edges. In some of these embodiments, bioFETS 125 are provided in arrays wherein the arrays are extended (have a greater extent) along the length of manipulation electrodes 137A.

Another type of manipulation electrode 137 is not covered by a passivation layer 135 (e.g., passivating dielectric) and can be configured for electrical contact with adjacent fluid, such as fluid in a fluid containment area 104. Manipulation electrodes 137B of FIG. 1B provide an example. Manipulation electrodes 137B can be operative as reference electrodes to fix the potential of a bulk fluid adjacent fluid gates 117, which can facilitate certain modes of detection. A composition of manipulation electrodes 137B can facilitate this functionality. In some embodiments, manipulation electrodes 137B comprise silver. In some embodiments, manipulation electrodes 137B comprise AgCl. These compositions can provide ions to an aqueous solution in contact with manipulation electrodes 137B.

Manipulation electrodes 137 may comprise of any suitable material. In some embodiments, manipulation electrodes 137 comprise polysilicon. In some embodiments, manipulation electrodes 137 comprise a metal. Passivation layer 135 for manipulation electrodes 137A can be any suitable dielectric. In some embodiments, passivation layer 135 is $SiO_2$.

Manipulation electrodes 137 can be connected to a power source in any suitable fashion. In some embodiments, manipulation electrodes 137 are powered through metal interconnect structure 144. In some other embodiments, however, manipulation electrodes 137 are coupled directly to an external power source. In some embodiments, manipulation electrodes 137 are coupled to bonding pads 157 that are isolated from metal interconnect structure 144. Bonding pads 157B of FIG. 1B provide an example of bond pads 157 that can be used in this way. Powering manipulation electrodes 137 externally allow manipulation electrodes 137 to be powered with high voltages. In some embodiments, device 100 includes a plurality of distinct bonding pads 157 for distinct groups of manipulation electrodes 137. In some embodiments, distinct power source are used to provide power at distinct frequencies.

Powering distinct groups of manipulation electrodes 137 with distinct voltages or frequencies can facilitate multiplexed detection. Other types of variations in manipulation electrodes 137 can be used to provide selectivity for particular analytes and thereby facilitate multiplexed detection. In some embodiments, device regions 126 vary in one or more of number, geometry, and type of manipulation electrodes 137. In some embodiments, a single device region 126 includes multiple types of manipulation electrodes 137, such as both reference and diversion electrodes.

In some embodiments, bond pads 157 are disposed in a peripheral region 162 of device 100. Active layer 155 can include a front side 142, which is a side of device layer 140 facing metal interconnect structure 144, and a back side 138, which is a side of device layer 140 on which fluid interfacing surfaces 122 are formed. In some embodiments, bond pads 157 are formed for connection on a side of device 100 correspond to back side 138. In some embodiments, some bond pads 157 connect to metal interconnect structure 144. Bond pads 157A of FIG. 1A provide an example. In some embodiments, bond pads 157A form connections to metal interconnect structure 144 through openings in semiconductor active layer 155. This configuration can allow device 100 to connect to an external device through connections on a side opposite a carrier substrate 147.

Bond pads 157 may include conductive landings operable to provide a region for wire bonding, ball or bump bonding, and/or other bonding techniques. Bond pads 157 can be operable to provide electrical connection to other electronic devices. Bond pads 157 can be of any suitable material. Examples include copper, aluminum, titanium, tungsten, alloys thereof, composites thereof, and combinations thereof. In some embodiments, bond pads 157 and manipulation electrodes 137 have the same composition.

In some embodiments, peripheral region 162 surrounds device regions 126. Peripheral region 162 may include column decoders (e.g., shown as element 163, row decoders 165 of FIG. 2) or other circuitry to drive and/or sense the state of bioFETs 125. Peripheral region 162 may include high voltage transistors and other suitable devices.

Metal interconnect structure 144 includes a plurality of layers. Each layer includes metal lines 149 in a matrix of dielectric 153. Adjacent layers are connected by metal-filled vias 151. In some embodiments, the dielectric 153 is a low-k dielectric and can be an extremely low-k dielectric. In some embodiments, the dielectric 153 is an extremely low-k dielectric, which is a low-k dielectric having porosity or air gaps that significantly reduce electrical and thermal conductivity. In some embodiments, metal lines 149 are copper. In some embodiments, there are five or more metal interconnect layers in metal interconnect structure 144.

In some embodiments, the layers of the metal interconnect structure 144 are scaled. Scaling is done by varying thickness and width of metal lines 149 among the metal interconnect layers. The lowest metal interconnect layers, which are closest to device layer 140, have the thinnest and narrowest metal lines 149 (wires). Metal lines 149 in the lowest layers have the highest RC delay and can be used to make local interconnections. In a scaled multilayer metal interconnect structure 144, wire thicknesses, widths, and separations gradually increase as additional metal interconnect layers are added. The topmost metal interconnect layers have the thickest, widest, and most coarsely spaced metal lines 149. The uppermost layers have the lowest RC delay and can be used for power and clock distribution and for global signal routing.

Figure 2:
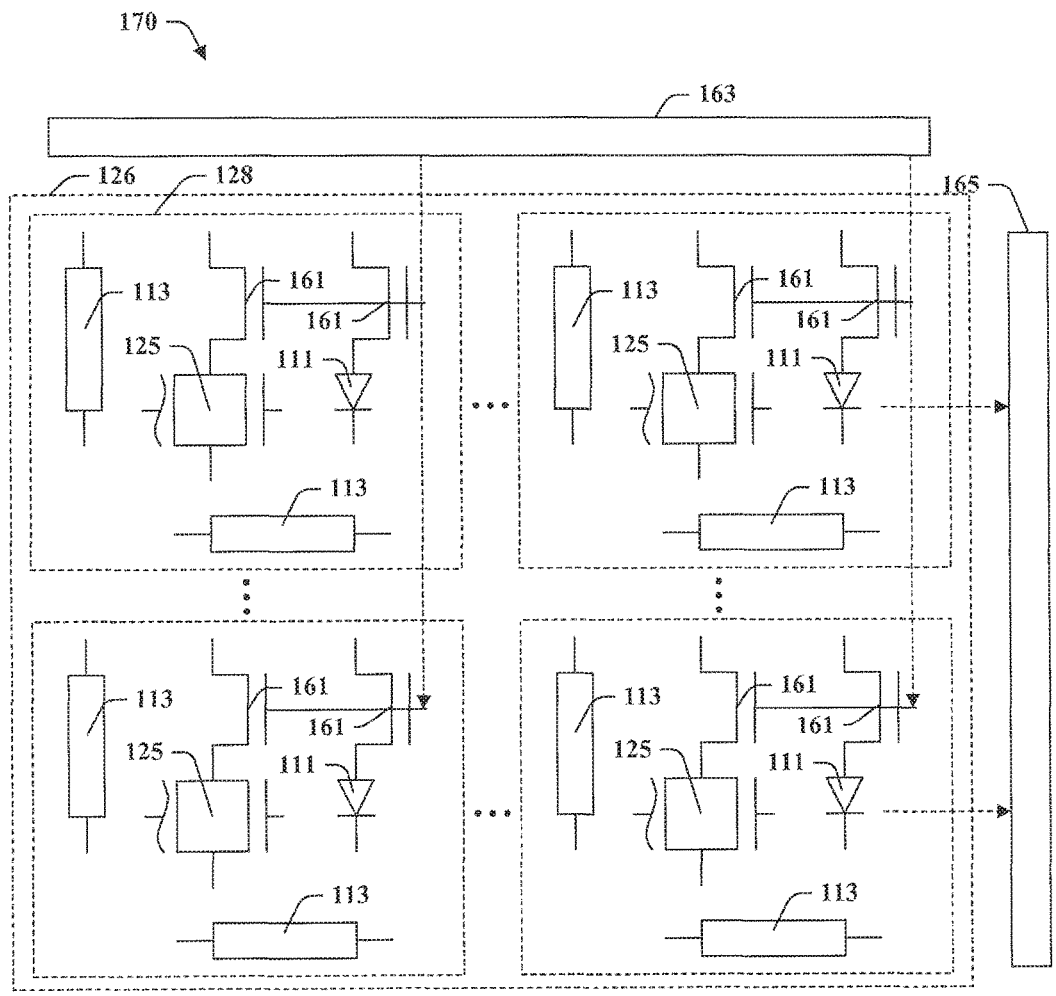
FIG. 2 is an example circuit diagram in accordance with some embodiments of the present disclosure.

FIG. 2 provides an example circuit 170 for a device region 126 according to some embodiments of the present disclosure.

Example circuit 170 includes an array of bioFETs 125, an array of temperature sensors 111, and a plurality of heating elements 113. In some embodiments, switches 161 are controlled by column decoders 163 and row decoders 165 to selectively address individual bioFETs 125 and temperature sensors 111 in the arrays. Column decoders 163 and row decoders 165 can be shared by the array of bioFETs 125 and the array of temperature sensors 111. In some embodiments, switches 161 of adjacent bioFETs 125 and temperature sensors 111 are coupled, whereby the selection to address a particular bioFET 125 in the array operates as a selection to address the paired temperature sensor 111 of the array.

In some embodiments, bioFETs 125 and temperature sensors 111 are provided in equal numbers. In some embodiments, device region 126 includes an array of pixels 128, each pixel including one bioFET 125 and one temperature sensor 111. In some embodiment, each pixel 128 includes at least one heating element 113. In some embodiments, each pixel 128 includes a plurality of heating elements 113. In some embodiments, a heating element 113 is located between each adjacent pair of bioFET 125 in device region 126. In some embodiments, heating element 113 surround on four sides each pixel 128 in an array of bioFETS 125.

In some embodiments, all the heating elements 113 in device region 126 are coupled, whereby they are controlled together. This configuration simplifies the control circuitry while still allowing the heating elements 113 of distinct device regions 126 to be controlled independently. In other embodiments, the heating elements 113 in device region 126 are coupled in a plurality of independent circuits, whereby different groups of heating elements 113 within a device region 126 can be controlled independently. This configuration may facilitate maintaining a uniform temperature across device regions 126. A uniform temperature would be one that varies by no more than 2° C. across a device region 126 at any given moment in time.

In some embodiments, a plurality of heating elements 113 are arrayed across device region 126. In some embodiments, heating elements 113 cover 10% or more of the area of device region 126. In some embodiments, heating elements 113 cover 25% or more of the area of device region 126. Covering a large fraction of the area to be heated with heating elements 113 facilitates the provision of a high heating rate while keeping current densities within acceptable limits.

Figure 3:
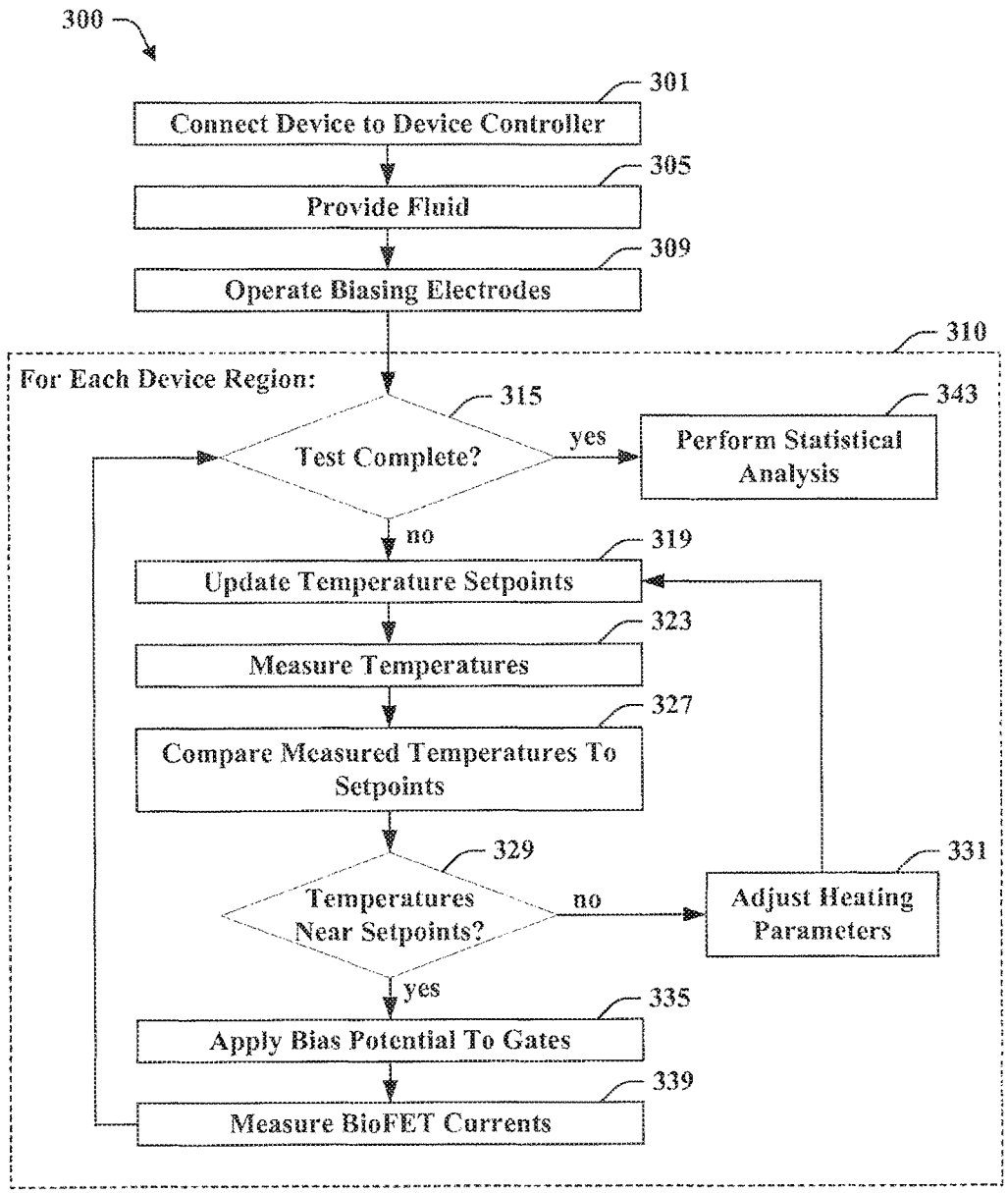
FIG. 3 is a flow chart of a diagnostic method in accordance with some embodiments of the present disclosure.

FIG. 3 is a flow chart of an example method 300 of using a device 100 according to some embodiments of the present disclosure. The method is described with respect to FIGS. 1A-1B.

Method 300 begins with action 301, connecting device 100 to a device controller. Action 301 can include connecting leads to bond pads 157. The device controller can be an external device that is adapted to receive devices 100 and perform one or more functions related to operating device 100. Those functions can include one or more of calibrating temperature sensors 111, storing calibration data, processing of data from temperature sensors 111, fluid handling, supplying power to device 100, operating electrodes 137, controlling heating elements 113, and receiving and interpreting data from bioFETs 125.

Method 300 proceeds with action 305, providing fluid to device 100. In some embodiments, the fluid is water with biological substances dissolved or suspended therein. In some embodiments, the fluid is one of blood, saliva, and urine. In some embodiments, supplying the fluid comprises operating micro-electro-mechanical systems (MEMs) that are incorporated into the device 100. In some embodiments, the MEMs include fluid pumps. In some embodiments, action 305 includes supplying the fluid to fluid containment areas 104. In some embodiments, action 305 includes supplying micro-droplets to a surface of device 100.

In some embodiments, method 300 continues with action 309, operating manipulation electrodes 137 to concentrate certain analytes proximate certain bioFETs 125. Action 309 is optional. In some embodiments, action 309 is carried out in some device regions 126. In some embodiments, action 309 is carried out in different ways for different device regions 126. The differences may relate to one or more of voltage applied to electrodes 137, whether that voltage is varied in a cyclical fashion, if the voltage is varied cyclically, the frequency of cycling, and the period over which the electrodes 137 are operated. In some embodiments, action 309 includes applying a reference voltage to electrodes 137B, which reference voltage is maintained through subsequent operations. In some embodiment, more than one set of electrodes 137 is present in a device region 126 and the different sets of electrodes 137 are operated differently.

Method 300 continues with a series of actions 310. The series of actions 310 can be performed in any suitable order and the order can vary among device regions 126. In some embodiments, the series of actions 310 are performed differently for each of a plurality of different groups of device regions 126. In some embodiments, the difference relate to the implementation of different testing protocols for the different groups of device regions 126.

The different testing protocols can be any testing protocols suitable for implementation on device 100. In some embodiments, one or more of the testing protocols includes initiating a heat mediated reaction. In some embodiments, one or more of the testing protocols includes detection of binding to a selective binding agent 119 and a variation of that binding with temperature. In some embodiments, one or more of the testing protocols includes sensing pH.

In some embodiments, one or more of the testing protocols includes hybridizing DNA and determining a degree of mismatch between a probe DNA and a sample DNA by determining a temperature dependence of disassociation of the hybridized DNA. In some embodiments, one or more of the testing protocols includes heat-mediated polymerase chain reaction (PCR).

In the example illustrated by FIG. 3, actions 310 begin with action 315, determining whether the testing protocol has been completed. If the testing protocol has been completed, method 300 can optionally proceed with action 343, performing statistical analysis. In some embodiments, there are a large number of device regions 126 in which a single protocol is executed. In some embodiment, each device region includes a large number of bioFETs 125 each having a fluid gate 117 with the same structure and functionality. Therefore, method 300 can produce a large number of data points related to a single point of inquiry and statistical analysis (action 343) may be desirable to fully interpret the output of device 100.

If the testing protocol is not complete, method 300 proceeds with action 319, updating a temperature set point. A temperature set point is a desired temperature for a device region 126. The temperature set point is a temperature currently called for by a testing protocol being implemented by actions 310. In some embodiments, the temperature set point varies over time. For example, heat-mediated PCR may include 10 or more cycles, e.g., 30 cycles, each cycle including a denaturing phase that includes holding a temperature of about 95° C. for a first period followed by a primer annealing phase that includes holding a temperature of 55° C. for a second period followed by an extension phase that includes holding a temperature of about 72° C. for a third period. The lengths of the periods may be measured from the time the temperature set points are reached. In some embodiments, device 100 is operative to rapidly adjust temperature in a small volume adjacent bioFETs 125, whereby device 100 is operative to complete a heat-mediated PCR cycle in 60 seconds or less. In some embodiments, device 100 is operative to complete a heat-mediated PCR cycle in 15 seconds or less.

Method 300 continues with action 323, obtaining temperature measurements from temperature sensors 111 and action 327, comparing the measured temperatures to the temperature set point for the device region 126. Action 329 is a decision step based on the comparison. If the measured temperatures are close to the set points, then method 300 continues with action 335. Otherwise, method 300 continues with action 331, which is adjusting operating parameters for heating elements 113 and operating heating elements 113 using those parameters. Actions 319 through 331 collectively provide a feedback control loop for temperature control within a device region 126. In some embodiments, the control loops are independent for each device region 126. Any suitable control algorithm can be employed. In some embodiments, a control algorithm includes proportional-integral-differential (PID) control. In some embodiments, the output of the control loop is a variation in the current through heating elements 113. In some embodiments, all the heating elements 113 within a device region 126 are controlled as a unit from a single current source. In some embodiments, some of the heating elements 113 in a device region 126 are controlled independently from other heating elements within the device region 126 to reduce temperature gradients across the device region 126.

Method 300 continues with action 335, applying a biasing potential to conventional gates 129 of bioFETs 125. Action 335 is optional and some bioFETs 125 may not include conventional gates 129. A biasing potential can be applied to conventional gates 129 to vary the sensitivity of bioFETs 125A to electric fields from fluid gates 117.

Action 339 is determining the states of bioFETs 125. The states may be characterized by source to drain currents, source to drain conductivities, or voltage outputs. These states of bioFETs 125 are modulated through fluid gates 117 to provide sensing functions of device 100.

Figure 4:
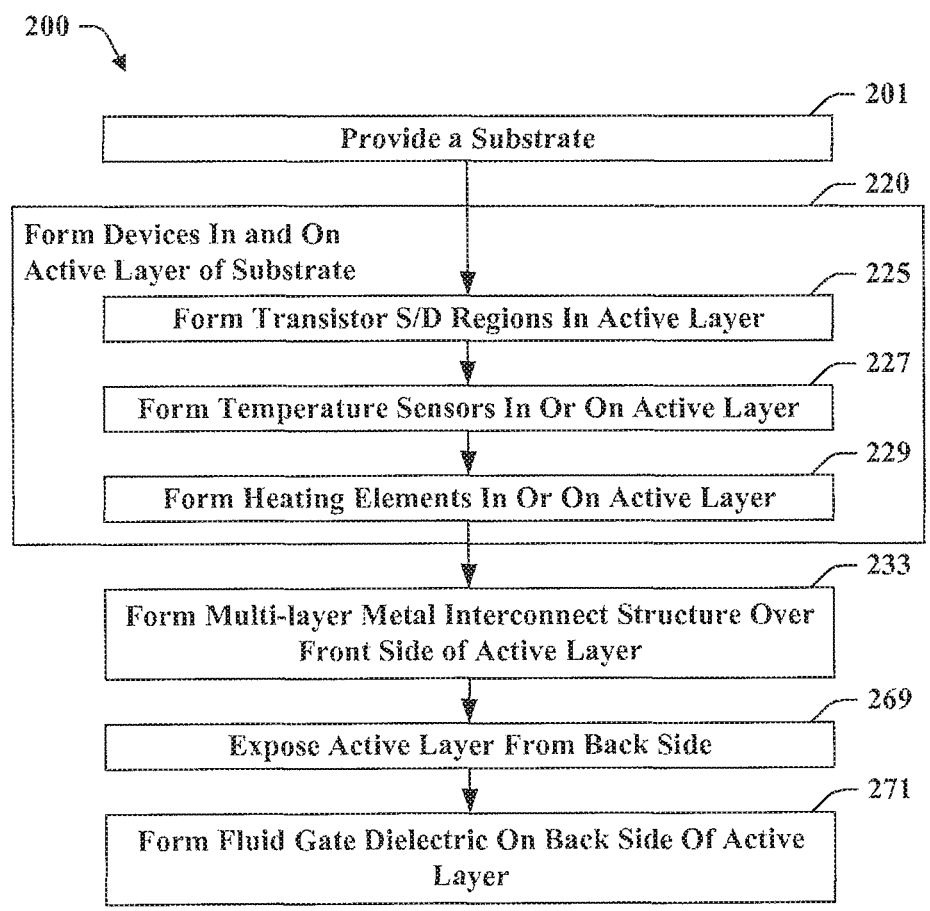
FIG. 4 is a flow chart of a method of manufacturing an integrated circuit device in accordance with some embodiments of the present disclosure.

FIG. 4 provides a flow chart of a method 200 of manufacturing an integrated circuit device according to some embodiments of the present disclosure. Method 200 begins with action 201, providing a substrate. In some embodiments, the substrate is a silicon-on-insulator (SOI) substrate.

Method 200 continues with a series of actions 220 that form devices in and on an active layer of the substrate. The actions within the series of actions 220 can be performed in any suitable order. The series of actions 220 include action 225, forming S/D regions for bioFETs in an active layer of the substrate, action 227, forming temperature sensors in or on the active layer, and action 229, forming heaters in or on the active layer.

Method 200 continues with action 233, forming a multi-layer metal interconnect structure over the active layer. An active layer has two sides, which can be referred to as a front side and a back side. The side of the active layer over which the multilayer metal interconnect structure is referred to herein as the front side. The terms "front" and "back" are therefore spatially relative terms used to distinguish references to the multilayer metal interconnect structure side of the active layer from the other side of the active layer. In some embodiments, the metal interconnect layers are formed by damascene or dual damascene processes.

Method 200 continues with action 269, exposing at least some areas of the active layer back side. The exposed areas can include channel regions of the active layer, which are areas between adjacent source/drain regions formed by action 225. In some embodiments, action 269 includes thinning the substrate. In some embodiments, after thinning the substrate is reduced to a thickness in the range from approximately 500 Angstroms (A) to approximately 1500 A. In some embodiments, thinning includes chemical mechanical polishing (CMP). In some embodiments, thinning include a wet etch process. Example of wet etchants that may be suitable for thinning the substrate include HNA (hydrofluoric, nitric, and acetic acid), tetramethylammonium hydroxide (TMAH), KOH, and buffered oxide etch (BOE). In some embodiments, thinning include a dry etch process.

In some embodiments, thinning proceeds to the extent of exposing the back side of the active layer. In some embodiments, instead of or in addition to thinning, action 269 includes forming openings through one or more layers on the back side of the substrate. The openings may be formed using photolithography and etching. The etching process can include wet etching or dry etching.

Method 200 continues with action 271, forming a fluid gate dielectric layer on exposed portions of the active layer back side. Method 200 thereby defines a process in which transistors having fluid gates, heating elements, and temperatures sensors are formed in a device layer with a multilayer metal interconnect structure on one side of the device layer and fluid gates of the transistors opening to the opposite side of the device layer.

Figure 5A:
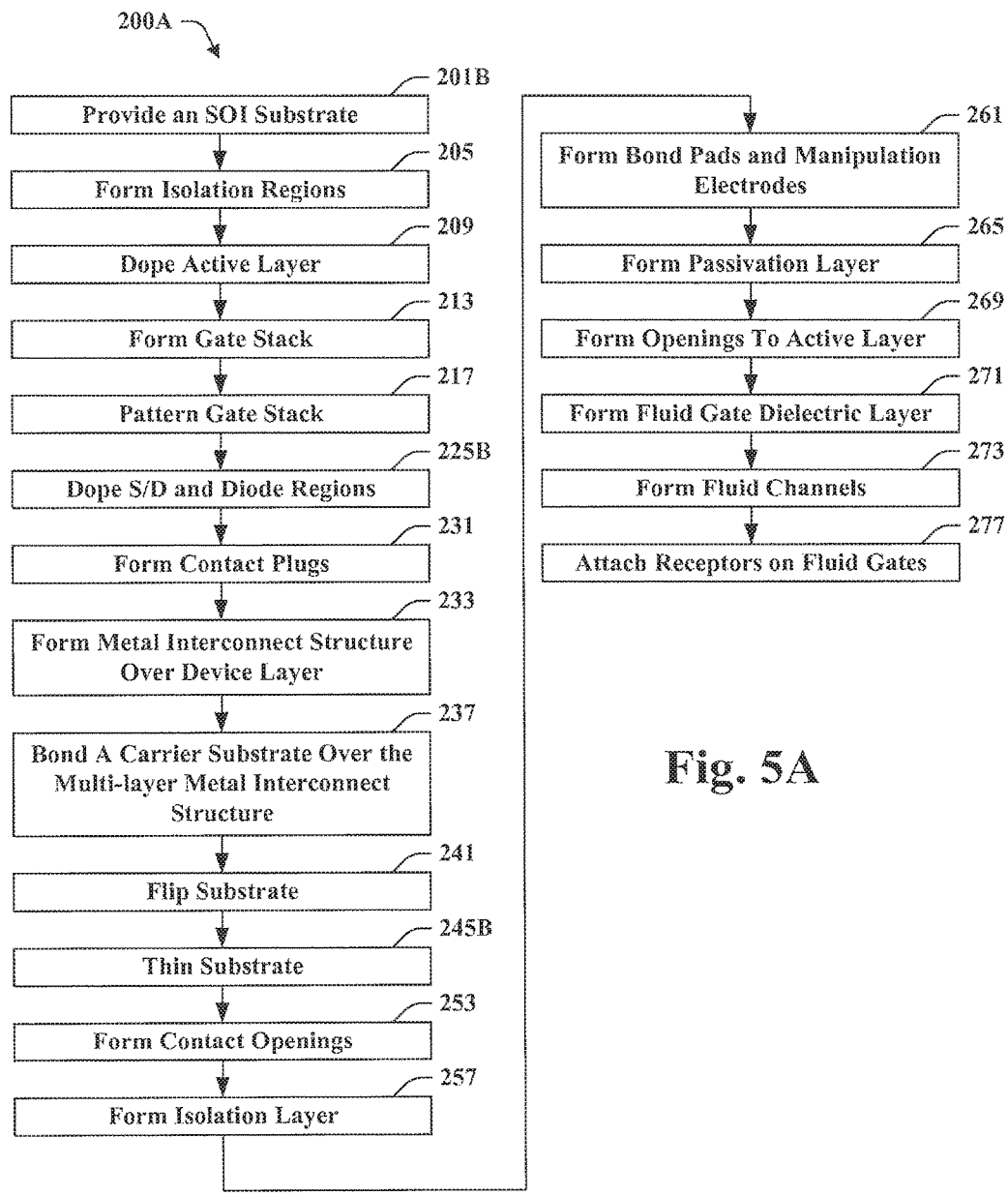
FIG. 5A is a flow chart of a method of manufacturing an integrated circuit device in accordance with some embodiments of the present disclosure.

FIG. 5 provides a flow chart of a method 200A, which is an example of method 200 in accordance with some embodiments of the present disclosure. In method 200A, the first action 201 is action 201B, providing an SOI substrate. An SOI substrate can include a semiconductor active layer over a buried oxide layer.

Method 200A continues with action 205, forming isolation regions in an active layer of the SOI substrate. Action 205 can include, for example, a masking and oxidation process to form field oxide areas or an etching and filling process to form STI regions.

Method 200A continues with action 209, doping the active layer. Action 209 can include doping to form n-doped and p-doped regions for a CMOS device. The doping of action 209 sets the conductivity for channel regions of transistors that will be formed into the active layer. In some embodiments, action 209 sets the conductivity for an n-doped or p-doped side of a temperature sensing diode.

Method 200A continues with action 213, forming a gate stack on the active layer. A gate stack can include a gate dielectric layer and a gate electrode layer. In some alternate embodiments, action 209 forms a dummy gate stack and method 200A is to define a gate replacement process. A gate replacement process can be desirable to provide conventional gates having metal electrodes.

Method 200A continues with action 217, patterning the gate stack. Action 217 can define the locations for transistors. In some embodiment, the patterned gate stack also provides the structure for heating elements. In some embodiment, the patterned gate stack also provides the structure for temperature sensors.

Action 225B is an embodiment of action 225 of method 200. Action 225B is doping the active layer to form temperature sensing diodes and transistor source/drain regions. In some embodiments, the patterned gate stack provides a mask for this process, making it a self-aligned doping process.

In some embodiments, action 225B forms source/drain regions having doping profiles that extend through the full thickness of an active layer of an SOI substrate. A suitable dopant dosage to form the source/drain regions can be in the range from about $10^{10}$ to about $10^{16}$ atoms per cubic centimeter. In some embodiments, the acceleration voltage or energy at which the dopants are supplied is in the range from about 20 keV to about 200 keV. In some embodiments, the dopant concentration in the source/drain region bordering the opposite side of the active layer from the one from which the dopants are supplied reaches into a ranges from about $10^{17}$ to about $10^{20}$ atoms per cubic centimeter. In some embodiments, the dopants for the source/drain regions are arsenic or phosphorous.

Action 231 forms contact plugs for devices in and on the active layer. Action 231 includes forming an inter-level dielectric layer over the active layer, forming vias in that inter-level dielectric layer, and filling the vias to form contact plugs. The contact plugs form connections with the source/drain regions. In some embodiments, the contact plugs also form connections with the temperature sensing diodes. In some embodiments, the contact plugs also form connections with the heating elements.

Method 200A continues with action 233, forming a multilayer metal interconnect structure over the active layer. The multilayer metal interconnect structure forms connection with the contact plugs formed by action 231.

Action 237 is bonding a carrier substrate over the multilayer metal interconnect structure. In some embodiments, action 237 includes forming electrical connections between the carrier substrate and the metal interconnect structure. In some other embodiments, the carrier substrate is electrically isolated from the multilayer metal interconnect structure.

Action 241 is flipping the substrate. Actions 205 through 233 can be convention CMOS processes. These processes are typically applied to one side of an SOI substrate, which can be referred to as a front side. Processing after action 241 in method 200A is generally applied to the opposite side of the SOI substrate. Action 241 can be a logical rather than a literal process.

Method 200A continues with action 245B, thinning the substrate. In some embodiments, the substrate is thinned such that a bulk layer of the substrate, which is the portion on an SOI substrate opposite the buried oxide layer from the semiconductor active layer, is removed. In some embodiments, removing the bulk layer includes CMP. In some embodiments, removing the bulk layer includes wet etching. Wet etching can be with HNA or TMAH, for example. In some embodiments, the thinning process removes the buried oxide layer. In some other embodiments, the thinning process stops in or on the buried oxide layer. In some embodiments, a first thinning process removes the bulk layer and stops at the buried oxide layer. The first thinning process may be followed by a second thinning process, such as a BOE wet etch, which removes the buried oxide and stops at the silicon of the active layer. In some embodiments, the thinning process ends within the buried oxide layer. In some embodiments, a portion of the buried oxide layer is left to operate as an isolation layer.

Method 200A continues with action 253, forming opening for contacts. The opening are formed from the back side of the substrate and penetrate the active layer to expose the multilayer metal interconnect structure. These openings can be formed by any suitable process. A suitable process can include forming a lithographic mask and etching.

Method 200A continues with action 257, forming a dielectric isolation layer over the back side of the substrate. In some embodiments, the dielectric isolation layer is formed by oxidation. In some embodiments, the dielectric isolation layer is formed by deposition. In some embodiments, the dielectric isolation layer formed at this stage of processing provides a fluid gate dielectric layer. In some embodiments, a masking and etching process is employed to remove the dielectric isolation layer at the base of the contact opening formed by action 253. In some embodiments, action 253, forming the openings for contacts, takes place after action 257, forming the dielectric isolation layer that can also provide a fluid gate dielectric layer.

Method 200A continues with action 261, depositing metal to form bond pads and manipulation electrodes. In some embodiments, action 261 includes forming a copper seed layer from which a copper layer is grown at the locations where the bond pads and the manipulation electrodes are desired.

Method 200A can continue with action 265, forming a passivation layer over some or all of the electrodes and at other locations where a dielectric passivation layer may be desired. Action 265 is optional.

Method 200A continues with action 269, forming openings to expose the active layer back side at locations where fluid gates are desired. Action 269 can include forming a mask and etching.

Method 200A continues with action 271, forming a fluid gate dielectric layer over the exposed portions of the active layer back side. In some embodiments, the fluid gate dielectric layer is removed from areas distal from the fluid gates. In some embodiments, the fluid gate dielectric layer is covered by an isolation layer at locations distal from the fluid gates.

Method 200A optionally continues with action 273, forming fluid channels on the back side of the device. In some embodiments, action 273 includes forming channel walls on the back side of the device. In some embodiments, action 273 includes attaching a mat to the backside of the device, wherein the mat provides the channel boundaries. In some embodiments, action 273 includes attaching a cap to the back side of the device.

Method 200A continues with action 277, attaching receptors to the fluid gate. In some embodiments, action 277 includes attaching different receptors to different gates. In some embodiments, receptors are attached to only some of the fluid gates. In some embodiments, action 277 is not required.

Figure 5B:
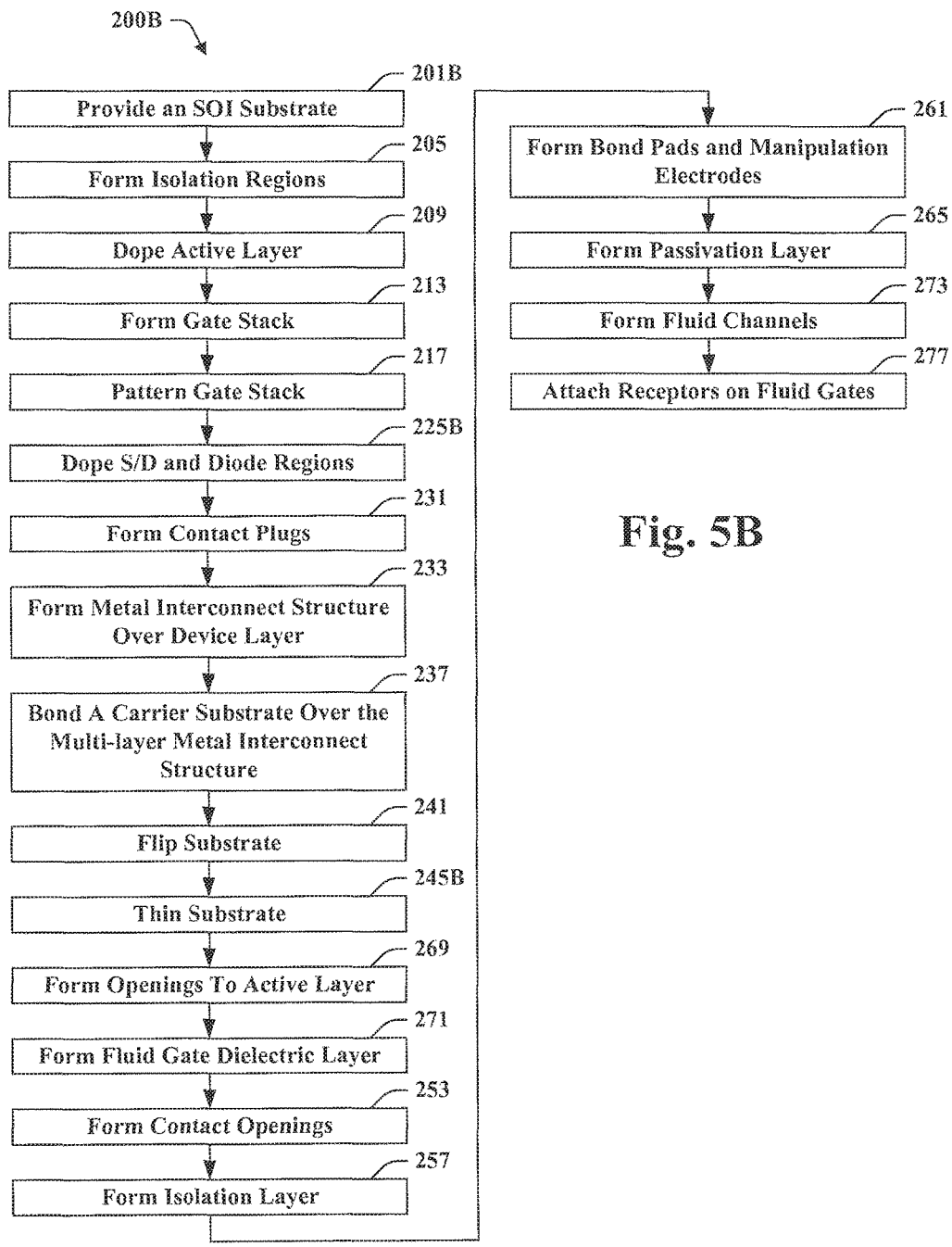
FIG. 5B is a flow chart of another method of manufacturing an integrated circuit device in accordance with some embodiments of the present disclosure.

FIG. 5B provides a flow chart of a method 200B, which is an alternative to method 200A that may have advantages, such as reduced contamination. Method 200B differs from method 200A in that action 269, forming openings to the active layer, and action 271, forming the fluid gate dielectric take place before action 253, forming contact openings, action 261, forming bond pads and manipulation electrodes, and action 265, forming a passivation layer.

While methods disclosed herein may be illustrated and described as a series of acts or events, the illustrated orderings are not exclusive of other embodiments. Some of the illustrated acts may occur in different orders and/or concurrently with other acts apart from the specifically described alternatives. Likewise, some of the illustrated acts not specifically identified as optional may not be required to provide processes and products according to the present disclosure.

FIGS. 6-21 illustrate device 100A of FIG. 1A undergoing manufacturing by method 200A of FIG. 5. Embodiments of the present disclosure shown by the structures of FIGS. 1A and 6-21 can be produced by other methods. Similarly, while FIGS. 6-21 illustrate some embodiments of method 200A, method 200A can be applied to produce other structures. Method 200A is not limited to the structures shown in FIGS. 6-21.

FIG. 6 illustrates a cross-sectional of an SOI substrate 145 provided by action 201B. SOI substrate 145 includes a semiconductor active layer 155, a buried oxide layer 167, and bulk semiconductor 169. The SOI substrate 145 can be formed by any suitable process. In some embodiments, SOI substrate 145 is formed through separation by implanted oxygen (SIMOX). In some embodiments, the SOI substrate 145 is in the form of a wafer. In this example, device 100A begins as SOI substrate 145.

FIG. 7 illustrates device 100A after action 205, forming isolation regions 101. FIG. 7 illustrates a patterned lithographic mask 124, which can be used to define a pattern in which isolation regions 101 are formed. In some embodiments, isolation regions 101 are formed through the full thickness of active layer 155.

FIG. 8 illustrates device 100A after action 209, doping the active layer 155. This process can take place before or after isolation regions 101 are formed. Mask 124 can be removed before or after action 209. In some embodiments, action 209 dopes to provide a desired conductivity in the doped areas of active layer 155 through the full thickness of active layer 155. Action 209 can include doping some areas of active layer 155 to a first conductivity type and other areas of active layer 155 to a second conductivity type to provide nMOS and pMOS regions.

FIG. 9 illustrates device 100A after action 213, forming a gate stack 136 over active layer 155. Gate stack 136 includes a gate dielectric 131 and a gate electrode layer 133. Gate stack 136 can include additional layers, such as an interfacial layer.

FIG. 10 illustrates device 100A after action 217, patterning the gate stack. A patterned mask 130 is shown having been formed over gate stack 136 and used as an etch mask to pattern the gates stack 136. In some embodiments, gate stack 136 is patterned to form gate 129 and heating elements 113A. Portions of gate stack 136 may also be left in place temporarily to be removed later after they have provided a mask for a subsequent doping step.

FIG. 11 illustrates device 100A after action 225B, doping to form S/D regions 115 and first diode regions 105. In some embodiments, a remaining portion of gate stack 136 masks second diode regions 107. First diode regions 105 and second diode regions 107 are of opposite conductivity types and interface to form P-N junction 106.

Figure 12:
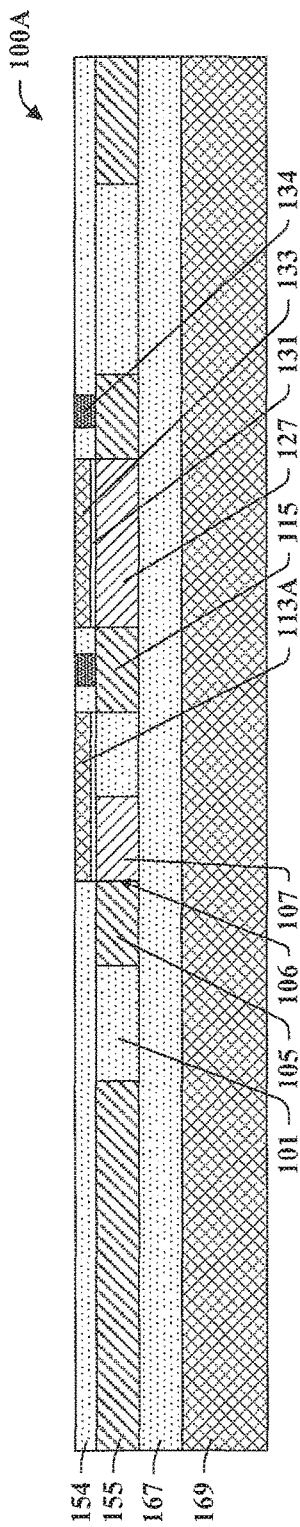

FIG. 12 illustrates device 100A after action 231, forming inter-level dielectric layer 154 with contact plugs 134. Contact plugs 134 make contact with S/D regions 115. In some embodiments, S/D regions 115 are salicided prior to forming contact plugs 134. In some embodiments, additional contact plugs 134 make connections with first diode regions 105 and/or second diode regions 107.

Figure 13:
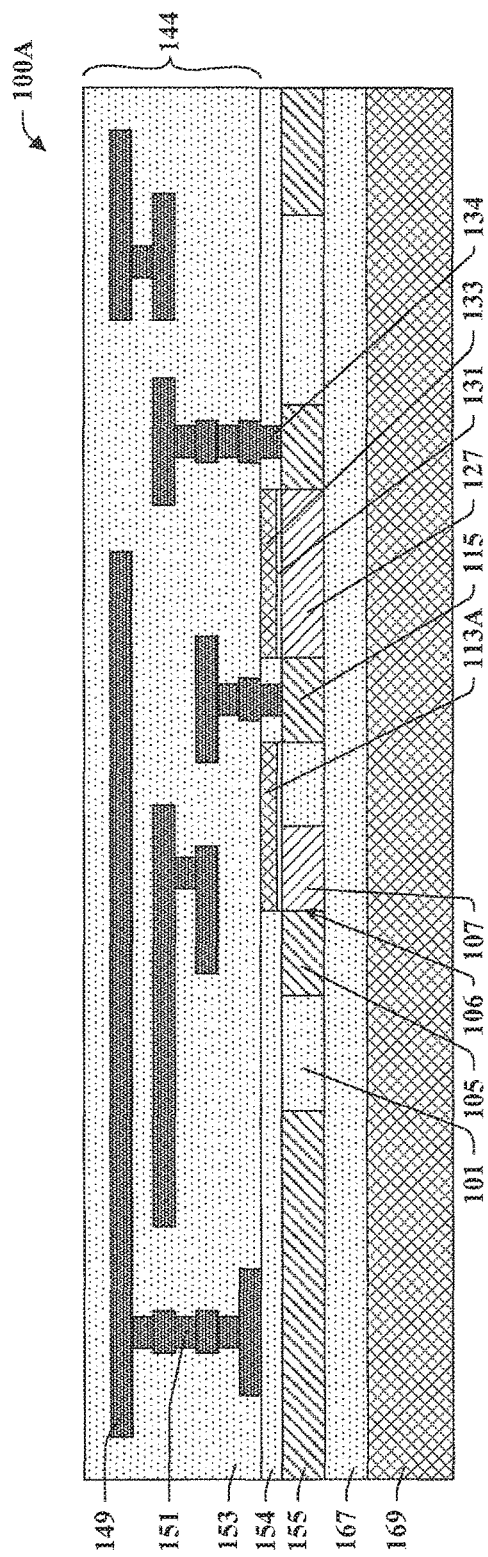

FIG. 13 illustrates device 100A after action 233, forming multilayer metal interconnect structure 144. Forming multilayer metal interconnect structure 144 can include sequentially forming multiple layers, each of which includes metal lines 149 and metal filled vias 151 in a matrix of dielectric 153. Dielectric 153 can include multiple layers of different materials. Metal interconnect structure 144 is shown schematically. The illustrations do not show all layers, connections, or layer scaling.

Metal lines 149 and vias 151 may be, for example, copper or aluminum. Dielectric 153 can be, for example, silicon dioxide, fluorinated silicon glass (FGS), SILK (a product of Dow Chemical of Michigan), BLACK DIAMOND (a product of Applied Materials of Santa Clara, Calif.), and/or other insulating material.

FIG. 14 illustrates device 100A after action 237, bonding carrier substrate 147 over metal interconnect structure 144. In some embodiments carrier substrate is bonded to dielectric 153. In some embodiments, carrier substrate 147 is bonded to a passivation layer formed on metal interconnect structure 144. Carrier substrate 147 may be bonded to device 100A by any suitable method. Examples of methods that may be suitable include fusion, diffusion, eutectic bonding methods.

Carrier substrate 147 can have any suitable compositions. In some embodiments, carrier substrate 147 includes a semiconductor. In some embodiments, carrier substrate 147 is glass or quartz. Carrier substrate 147 can provide structural stability during subsequent processing, such as action 245B, thinning. In some embodiments, carrier substrate 147 is removed some time after action 245B, thinning. In some embodiments, carrier substrate 147 provides other functionality. In some embodiments, carrier substrate 147 provides interconnect features. In some embodiments, carrier substrate 147 provides contact pads.

FIG. 15 illustrates device 100A after action 245B, thinning SOI substrate 145. In some embodiments, thinning removes bulk semiconductor 169 and buried oxide layer 167 as shown in this example.

Figure 16:
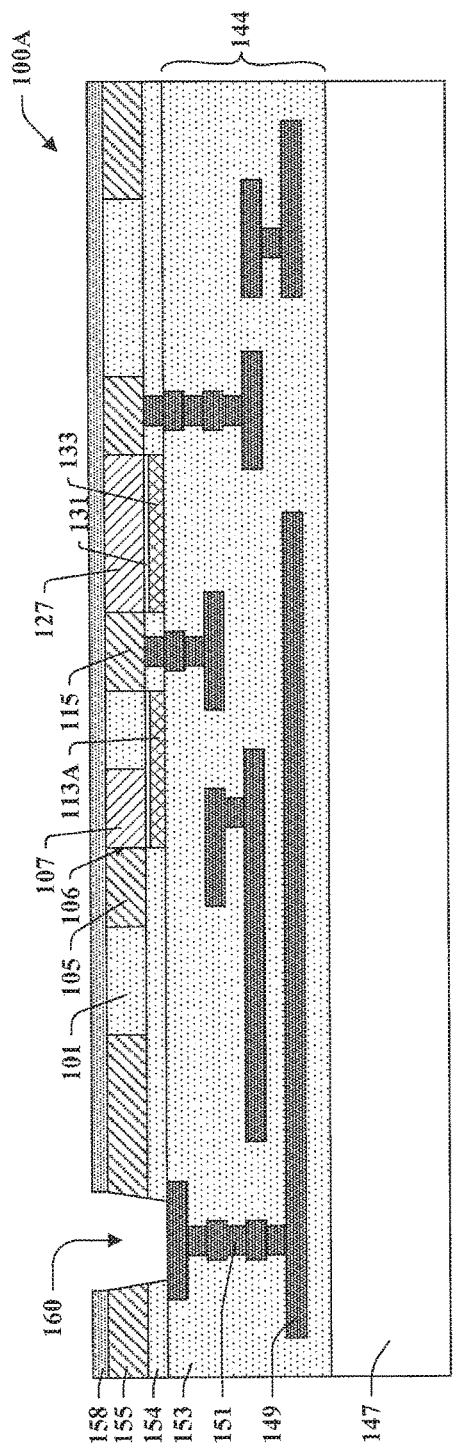

FIG. 16 illustrates device 100A after action 253, forming contact opening 160. Contact openings 160 is an opening through active layer 155 and can expose one or more of the metal lines 149 in metal interconnect structure 144. Contact openings 160 can be formed by any suitable process. A suitable process may include photolithography and etching (according to masking layer 158).

Figure 17:
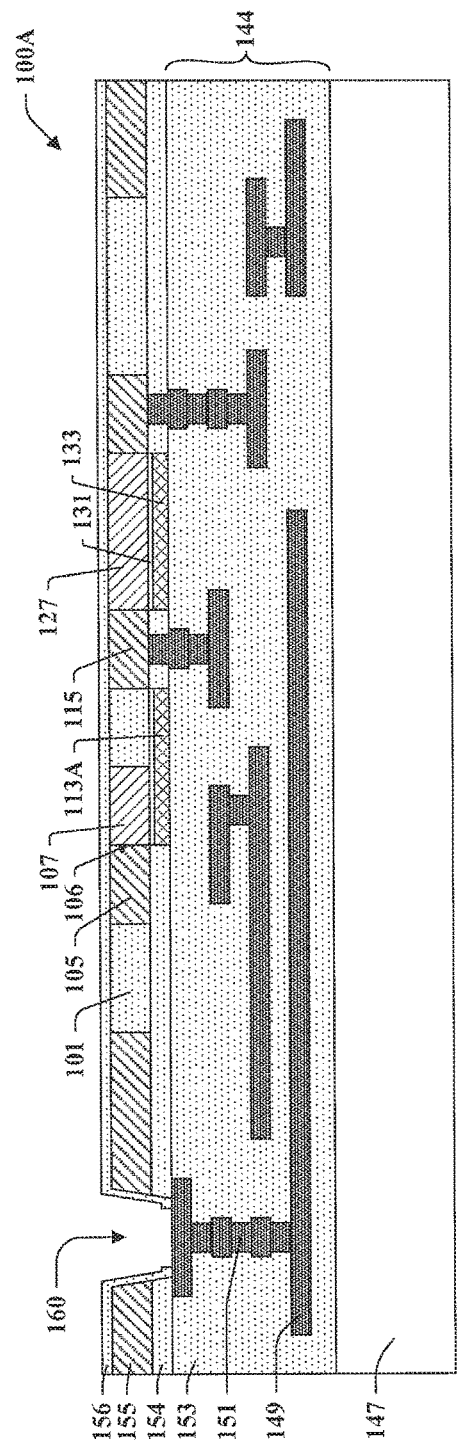

FIG. 17 illustrates device 100A after action 253, forming a layer of isolation dielectric 156 over the device 100A. Isolation dielectric 156 can include a dielectric oxide or nitride. In some embodiments, the isolation dielectric 156 is silicon oxide. An additional masking and etching process may be carried out to expose a metal line 149 of metal interconnect structure 144 at the base of contact opening 160A.

Figure 18:
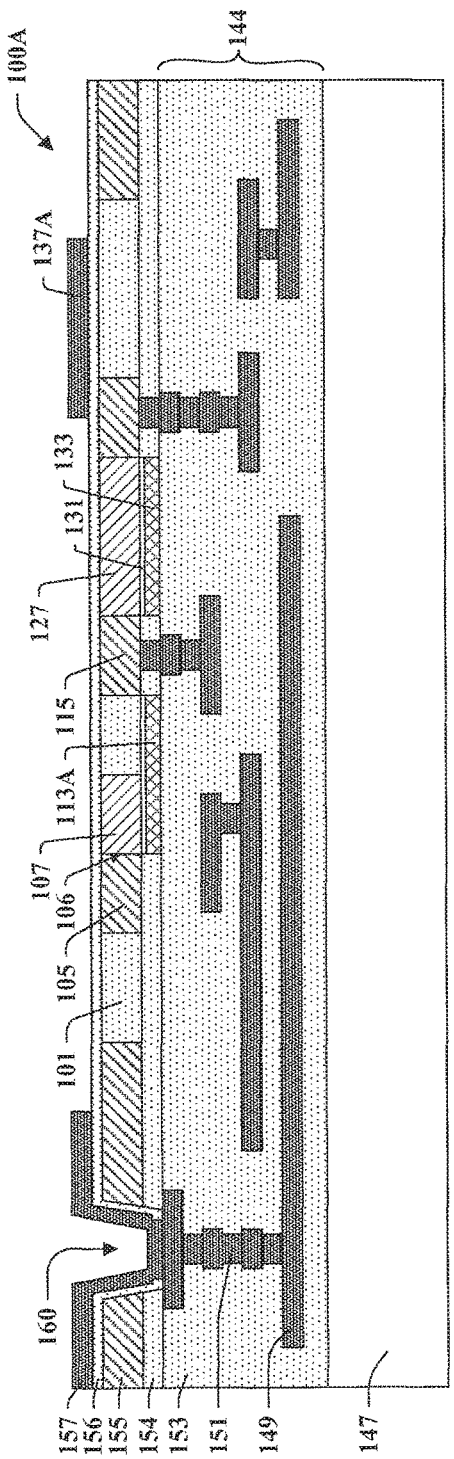

FIG. 18 illustrates device 100A after action 261, forming bond pads 157 and manipulation electrodes 137A. In some embodiments, manipulation electrodes 137A are formed over isolation dielectric 156. In some embodiments, bond pads 157 and manipulation electrodes 137A are formed from a patterned metal layer. In some embodiments, the metal is copper, aluminum, or an alloy of copper or aluminum. In some embodiments, bond pads 157 electrically couple with metal interconnect structure 144.

Figure 19:
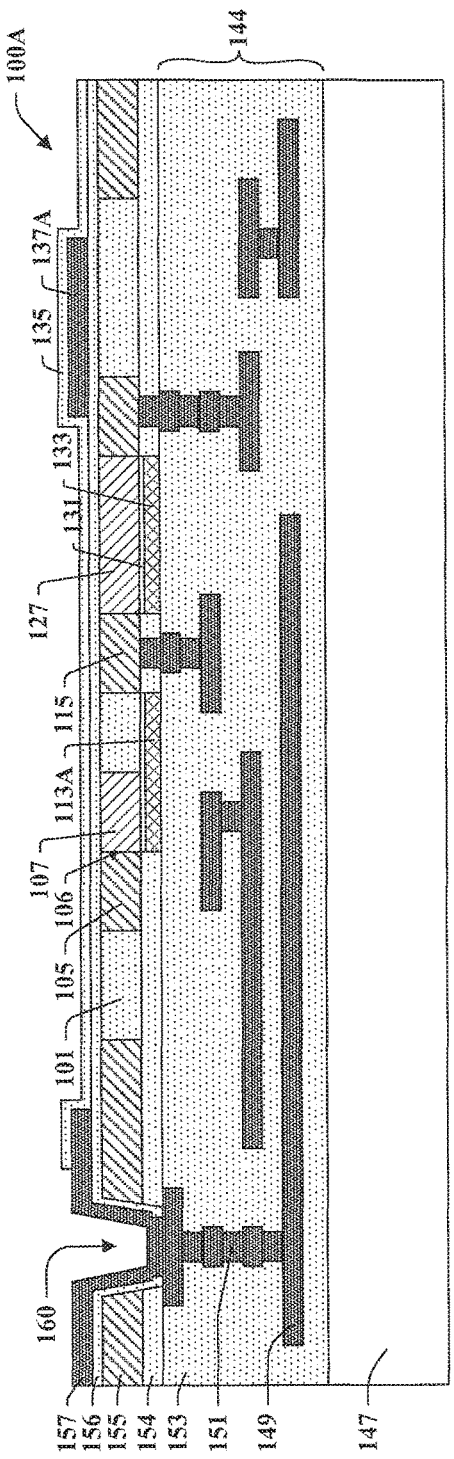

FIG. 19 illustrates device 100A after action 265, forming passivation layer 135. In some embodiments, passivation layer 135 covers and insulates at least some manipulation electrodes 137A. Passivation layer 135 may include openings over bond pads 157. In some embodiments, action 265 includes an additional mask and etch operation to remove passivation layer 135 from a surface of bond pads 157. In some embodiments, passivation layer 135 is functional to protect device 100 from moisture. Passivation layer 135 can be formed of any suitable dielectric or combination of dielectric layers. In some embodiments, passivation layer 135 is formed after fluid gate dielectric layer 121 and passivation layer 135 covers fluid gate dielectric layer 121 at locations distal from fluid gates 117. In some embodiments, passivation layer 135 includes a coating to block analytes from binding to its surface. In some embodiments, the coating includes bovine serum albumin (BSA) or a like substance.

Figure 20:
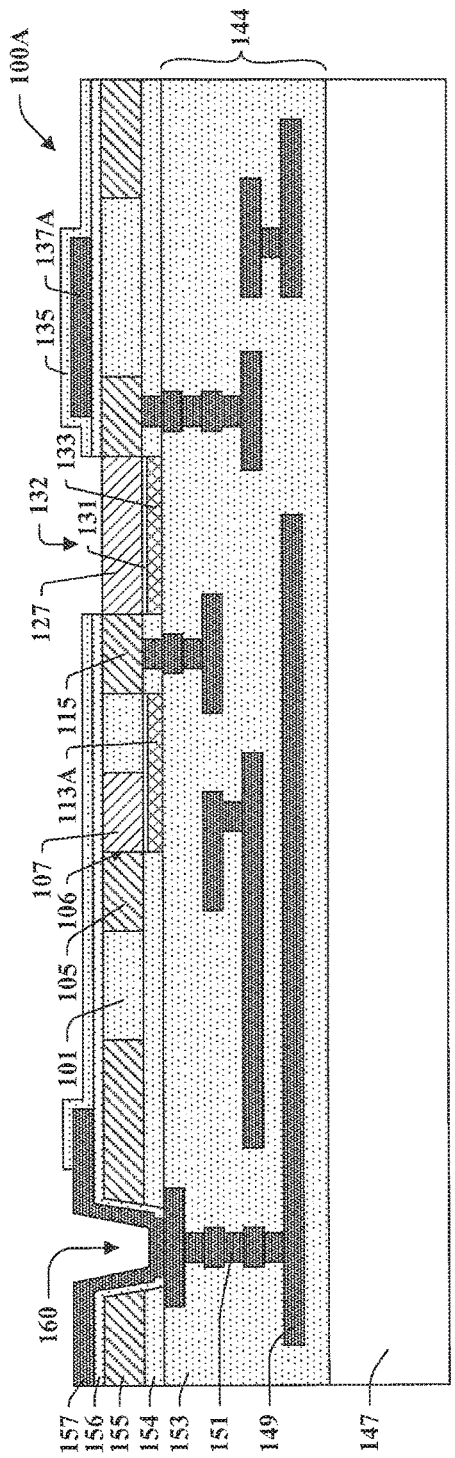

FIG. 20 illustrates device 100A after action 265, forming an opening 132 over active layer 155 at locations for channel regions 127. In some embodiments, opening 132 expose active layer 155. In some other embodiments, fluid gate dielectric layer 121 is formed earlier in the process sequence, and action 265 exposes fluid gate dielectric layer 121 over channel regions 127. In some embodiments, openings 132 are openings through isolation dielectric 156. In some embodiments, openings 132 are openings through passivation layer 135. Openings 132 may be formed by any suitable process. A suitable process can include photolithography and etching.

In some embodiment, action 265 forms one opening 132 for each biofet 125. In some embodiments, openings 132 are aligned with the transistor gate structure defined by source/drain regions 115. In some embodiments, openings 132 form an array with center-to-center spacing in a range from 30 to 300 nm. In some embodiments, openings 132 each have an area in the range from 0.10 to 10 nm$^2$.

Figure 21:
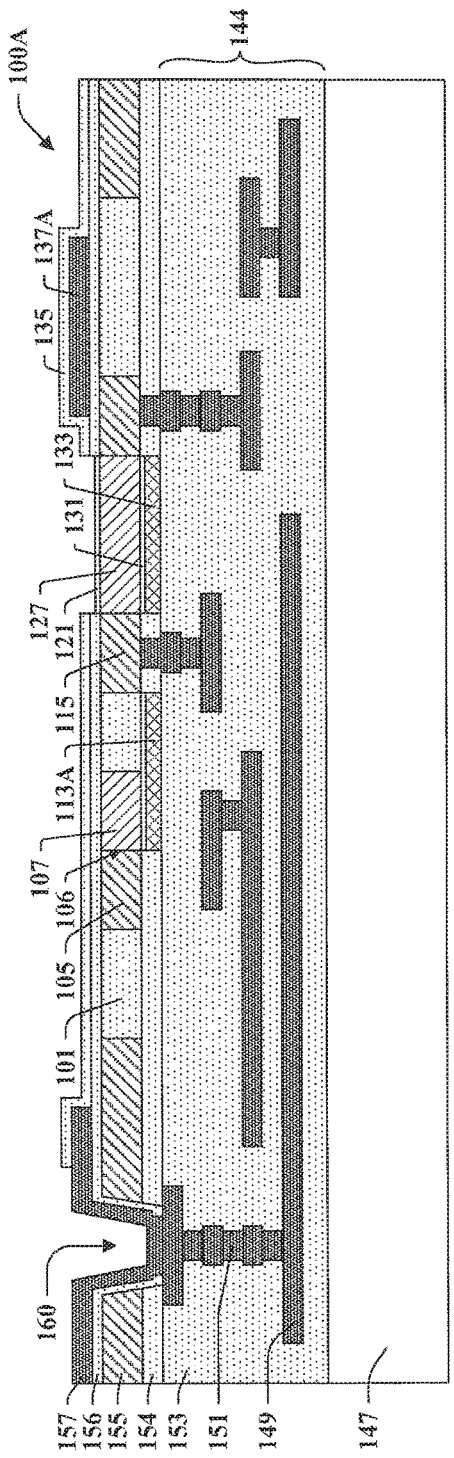

FIG. 21 illustrates device 100A after action 271, forming fluid gate dielectric layer 121. In some embodiments, fluid gate dielectric layer 121 is formed on active layer 155 immediate after active layer 155 is exposed by action 245B, thinning substrate 145. In some embodiments, fluid gate dielectric layer 121 is formed on active layer 155 immediate after action 245B, but before action 265, forming isolation dielectric 156. In some embodiments, fluid gate dielectric layer 121 and isolation dielectric 156 are the same layer. In some embodiments, fluid gate dielectric layer 121 is formed before passivation layer 135, whereby passivation layer 135 blocks adhesion of fluid born substances to fluid gate dielectric layer 121 at locations distal from fluid gates 117.

In some embodiments, fluid gate dielectric layer 121 includes a high-k dielectric material that is also effective for protecting underlying devices from moisture. High-k dielectric materials generally have a higher density and lower porosity than SiO$_2$. Examples of high-k dielectrics that can be effective for this purpose include HfO$_2$, Ta$_2$O$_5$, and Al$_2$O$_3$.

Fluid gate dielectric layer 121 can include a plurality of layers, only some of which are dielectric. In some embodiments, fluid gate dielectric layer 121 includes a metal coating. In some embodiments, the metal is Pt, Au, Al, W, Cr, or Cu. In some embodiments, fluid gate dielectric layer 121 has a diamond coating. In some embodiments, fluid gate dielectric layer 121 includes a silicon nitride layer. These layers can provide specialized sensing functionality.

The one or more layers of fluid gate dielectric layer 121 can be formed by any suitable processes. In some embodiments, fluid gate dielectric layer 121 is removed from areas distal from fluid gates 117. In some embodiments, fluid gate dielectric layer 121 received a protective coating while it is etched away from those distal locations. In some embodiments, fluid gate dielectric layer 121 is covered by passivation layer 135 at locations distal from fluid gates 117. Selective binding agents 119 (i.e., receptors) are optionally attached to fluid gate dielectric layer 121 at this or a later point in process 200A.

FIG. 1A illustrates device 100A after action 273, forming fluid channel walls 103. In some embodiments, fluid channel walls 103 include an elastomer. In some embodiments, the elastomer is polydimethylsiloxane (PDMS). In some embodiments, a layer of elastomer is patterned and then attached to device 100A to fluid channel walls 103. In some embodiments, the material of fluid channel walls 103 is first deposited and then pattern on the device 100A.

Therefore, the present disclosure relates to an integrated circuit device in which heaters and temperature sensors are formed into a device layer that also includes bioFETs.

One aspect of the present disclosure provides an integrated circuit device having a plurality of device regions. A device layer, which includes a front side, a back side, and a semiconductor active layer, spans the plurality of device regions. A multilayer metal interconnect structure is disposed on the front side of the device layer. Each of the device regions has one or more heating elements, one or more temperature sensors, and one or more field effect transistors in the device layer. The field effect transistors have source/drain regions and channel regions in the semiconductor active layer and fluid gates exposed on a surface for fluid interfacing on the back side of the device layer. This device structure enables precision and multiplexed temperature control when the device is used in sensing applications.

Another aspect of the present disclosure provides an integrated circuit device having an array of bioFETs including a first side and a second side. The second side is on the opposite side of the array from the first side. The bioFETs include a fluid gate dielectric. A multilayer metal interconnect structure is formed on the second side of the arrays. Heaters are formed between the multilayer metal interconnect structure and the first side of the array (in the array, or on its second side). Temperature sensors are also located between the multilayer metal interconnect structure and the first side of the array. The fluid gate dielectric is exposed for fluid contacting on the first side of the array. The bioFETs, the heaters, and the temperature sensors electrically interface with the multilayer metal interconnect structure.

Another aspect of the present disclosure provides a method of manufacturing an integrated circuit device. The method includes providing a substrate that has a semiconductor active layer having a front side and a back side. Source/drain regions, temperature sensors, and heating elements are formed in the semiconductor active layer and on its front side. This defines channel regions in the semiconductor active layer, which are regions between adjacent source/drain regions. A metal interconnect structure is formed over the front side. The metal interconnect structure is formed with contacts for the source/drain regions, the temperature sensors, and the heating elements. After the metal interconnect structure is formed, the channel regions are exposed from the back side of the substrate. A fluid gate dielectric over the exposed channel regions. In some embodiments, gates are formed over the channel regions by the same process steps that form heating elements on the back side of the active layer. In some embodiments, the heating elements are formed in the active layer by the same process steps that form the source/drain regions.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of manufacturing an integrated circuit device, comprising:
   providing a substrate comprising a semiconductor active layer having a front side and a back side;
   forming source/drain regions, temperature sensors, and heating elements either in the semiconductor active layer or on the front side of the semiconductor active layer, wherein channel regions are formed in the semiconductor active layer between adjacent source/drain regions, and wherein each of the heating elements is aligned over at least a portion of a corresponding temperature sensor;
   forming a metal interconnect structure over the front side of the semiconductor active layer, wherein the metal interconnect structure forms contacts with the source/drain regions, the temperature sensors, and the heating elements;
   exposing the channel regions from the back side of the semiconductor active layer; and
   forming a fluid gate dielectric over the exposed channel regions.

2. The method according to claim 1, further comprising:
   prior to forming the metal interconnect structure, forming a gate stack over the semiconductor active layer; and
   patterning the gate stack to form gate electrodes and the heating elements.

3. The method according to claim 1, further comprising:
   prior to forming the metal interconnect structure, forming a gate stack over the semiconductor active layer; and
   patterning the gate stack to form gate electrodes and the temperature sensors.

4. The method according to claim 1, wherein the source/drain regions and the heating elements are formed simultaneously by doping portions of the semiconductor active layer.

5. The method according to claim 1, wherein the source/drain regions and the temperature sensors are formed simultaneously by doping portions of the semiconductor active layer.

6. The method according to claim 1, wherein forming the temperature sensors comprises masking a portion of the temperature sensors with corresponding heating elements during a doping of the semiconductor active layer.

7. The method according to claim 1, wherein forming the fluid gate dielectric comprises forming an ion sensing film.

8. A method of manufacturing an integrated circuit device, comprising:
   providing a substrate comprising a device layer;
   forming source/drain regions, temperature sensors, and heating elements in the device layer, wherein channel regions are formed in the device layer between adjacent source/drain regions, and wherein each of the heating elements is aligned over at least a portion of a corresponding temperature sensor;
   forming a metal interconnect structure over a front side of the device layer, wherein the metal interconnect structure forms contacts with the source/drain regions, the temperature sensors, and the heating elements;
   exposing the channel regions from a back side of the device layer; and
   forming a fluid gate dielectric over the exposed channel regions.

9. The method according to claim 8, further comprising:
   prior to forming the metal interconnect structure, forming a gate stack in the device layer; and
   patterning the gate stack to form gate electrodes and the heating elements.

10. The method according to claim 8, further comprising:
    prior to forming the metal interconnect structure, forming a gate stack in the device layer; and
    patterning the gate stack to form gate electrodes and the temperature sensors.

11. The method according to claim 8, wherein the source/drain regions and the heating elements are formed simultaneously by doping portions of the device layer.

12. The method according to claim 8, wherein the source/drain regions and the temperature sensors are formed simultaneously by doping portions of the device layer.

13. The method according to claim 8, wherein forming the temperature sensors comprises masking a portion of the temperature sensors with corresponding heating elements during a doping of the device layer.

14. The method according to claim 8, wherein forming the fluid gate dielectric comprises forming an ion sensing film.

15. A method of manufacturing an integrated circuit device, comprising:
    providing a substrate comprising a semiconductor active layer having a front side and a back side;
    forming a heating element on a front side of the semiconductor active layer;
    forming source/drain regions and a temperature sensor in the semiconductor active layer, wherein the temperature sensor is formed such that the heating element is aligned over at least a portion of the temperature sensor;
    exposing a portion of the semiconductor active layer between the source/drain regions from a back side of the semiconductor active layer; and
    forming a fluid gate dielectric over the exposed portion of the semiconductor active layer.

16. The method according to claim 15, further comprising:
    prior to forming the metal interconnect structure, forming a gate stack over the semiconductor active layer; and
    patterning the gate stack to form gate electrodes and the heating element.

17. The method of claim 15, wherein forming the temperature sensor comprises forming two diodes in the semiconductor active layer.

18. The method according to claim 15, wherein the source/drain regions and the temperature sensors are formed simultaneously by doping portions of the semiconductor active layer.

19. The method according to claim 15, wherein forming the temperature sensor comprises masking a portion of the temperature sensor with the heating element during a doping of the semiconductor active layer.

20. The method according to claim 15, wherein forming the fluid gate dielectric comprises forming an ion sensing film.

\* \* \* \* \*